US005488099A

United States Patent [19]

Persson et al.

[11] Patent Number: 5,488,099
[45] Date of Patent: Jan. 30, 1996

[54] MULTIFUNCTIONAL CHIMERIC NEUROTROPHIC FACTORS

[76] Inventors: Hakan B. Persson, deceased, Vreta Gard, late of S-14743 Tumba, by Katherine Rowe McIntyre; Carlos F. I. Moliner, Tangvagen 29, S-12638 Hagersten, both of Sweden

[21] Appl. No.: 979,630

[22] Filed: Nov. 20, 1992

Related U.S. Application Data

[63] Continuation-in-part of Ser. No. 847,369, Mar. 6, 1992, Pat. No. 5,349,055.

[51] Int. Cl.$^6$ ........................ C07K 14/475; C07K 14/48

[52] U.S. Cl. ..................... 530/399; 435/69.1; 435/320.1; 536/23.5

[58] Field of Search ........................... 530/399; 435/69.1, 435/320.1; 536/23.5

[56] References Cited

PUBLICATIONS

Klein et al. *Cell* 66:395–403 (1991).
Ibanez et al. *EMBO J.* 9(5):1447–83 (1990).
Ibanez et al. *EMBO J* 10(8):2105–10 (1991).
Suter et al. *J. Neurosci.* 12(1):306–18 (1992).
Leibrock et al. *Nature* 341:149–52 (1989).
Glass et al. *Cell* 66:405–13 (1991).
Kaplan et al. *Nature* 350:158–160 (1991).
Soppet et al. *Cell* 65:895–903 (1991).
Barinaga M. *Science* 264:772–774 (1994).

*Primary Examiner*—Garnette D. Draper
*Assistant Examiner*—Shelly Guest Cermak
*Attorney, Agent, or Firm*—Gail M. Kempler

[57] ABSTRACT

Neurotrophins having activities of multiple parental neurotrophins are described, as well as DNA for their production and pharmaceutical preparations thereof.

4 Claims, 15 Drawing Sheets

Fig.1A.

| | NH2 | | I | | IIa | IIb | |
|---|---|---|---|---|---|---|---|
| NGF | SSTHPVFHM | GEFSVCDSVSVWV | G--DKTTATD I KGKE | VTVL | GEVN I | NNSVF | KQYFFETKC |
| BDNF | --HSDPARR | . . L . . . . . . I . E . . | TAA . . K . . V . MS . GT | . . . . | EK . PV | SKGQL | . . . . Y . . . . |
| NT-3 | -YAEHKS . R | . . Y . . . . . . E . L . . | T-- . . SS . I . . . R . BQ | . . . . | . . . I KT | G . . PV | . . . . Y . . R . |

| | III | | IV | | V | | COOH |
|---|---|---|---|---|---|---|---|
| NGF | RAPNPVES | GCRG I DSKHWSN | YCTTTHTFVK | ALTTD | DKQ - AA | WRFIRIDTACVC | VLSRKAARRG |
| BDNF | NPMGYTKE | . . . . . . . KR . . . . | Q . R . . QSY . R | . . . M . | S . KR I G | . . . . . . . . S . . . | T . TI . RG . -- |
| NT-3 | KEAR . . KN | . . . . . . . D . . . NS | Q . K . SQ . Y . R | . . . SE | NNK LVG | . . W . . . . S . . . | A . . . . I G . T- |

SEQUENCE LISTING ( 1 ) GENERAL INFORMATION:

( i i i ) NUMBER OF SEQUENCES: 3

-continued ( 2 ) INFORMATION FOR SEQ ID NO:1:

( i ) SEQUENCE CHARACTERISTICS:
( A ) LENGTH: 120 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:1:

| | | | | | | | | | | | | | | | |
|---|---|---|---|---|---|---|---|---|---|---|---|---|---|---|---|
| Ser | Ser | Thr | His | Pro | Val | Phe | His | Met | Gly | Glu | Phe | Ser | Val | Cys | Asp |
| 1 | | | | 5 | | | | | 10 | | | | | 15 | |
| Ser | Val | Ser | Val | Trp | Val | Gly | Asp | Lys | Thr | Thr | Ala | Thr | Asp | Ile | Lys |
| | | | 20 | | | | | 25 | | | | | 30 | | |
| Gly | Lys | Glu | Val | Thr | Val | Leu | Gly | Glu | Val | Asn | Ile | Asn | Asn | Ser | Val |
| | | 35 | | | | | 40 | | | | | 45 | | | |
| Phe | Lys | Gln | Tyr | Phe | Phe | Glu | Thr | Lys | Cys | Arg | Ala | Pro | Asn | Pro | Val |
| | 50 | | | | | 55 | | | | | 60 | | | | |
| Glu | Ser | Gly | Cys | Arg | Gly | Ile | Asp | Ser | Lys | His | Trp | Ser | Asn | Tyr | Cys |
| 65 | | | | | 70 | | | | | 75 | | | | | 80 |
| Thr | Thr | Thr | His | Thr | Phe | Val | Lys | Ala | Leu | Thr | Thr | Asp | Asp | Lys | Gln |
| | | | | 85 | | | | | 90 | | | | | 95 | |
| Ala | Ala | Trp | Arg | Phe | Ile | Arg | Ile | Asp | Thr | Ala | Cys | Val | Cys | Val | Leu |
| | | | 100 | | | | | 105 | | | | | 110 | | |
| Ser | Arg | Lys | Ala | Ala | Arg | Arg | Gly | | | | | | | | |
| | | 115 | | | | | 120 | | | | | | | | |

( 2 ) INFORMATION FOR SEQ ID NO:2:

( i ) SEQUENCE CHARACTERISTICS:
( A ) LENGTH: 119 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| His | Ser | Asp | Pro | Ala | Arg | Arg | Gly | Glu | Leu | Ser | Val | Cys | Asp | Ser | Ile |
| 1 | | | | 5 | | | | | 10 | | | | | 15 | |
| Ser | Glu | Trp | Val | Thr | Ala | Ala | Asp | Lys | Lys | Thr | Ala | Val | Asp | Met | Ser |
| | | | 20 | | | | | 25 | | | | | 30 | | |
| Gly | Gly | Thr | Val | Thr | Val | Leu | Glu | Lys | Val | Pro | Val | Ser | Lys | Gly | Gln |
| | | 35 | | | | | 40 | | | | | 45 | | | |
| Leu | Lys | Gln | Tyr | Phe | Tyr | Glu | Thr | Lys | Cys | Asn | Pro | Met | Gly | Tyr | Thr |
| | 50 | | | | | 55 | | | | | 60 | | | | |
| Lys | Glu | Gly | Cys | Arg | Gly | Ile | Asp | Lys | Arg | His | Trp | Ser | Asn | Gln | Cys |
| 65 | | | | | 70 | | | | | 75 | | | | | 80 |
| Arg | Thr | Thr | Gln | Ser | Tyr | Val | Arg | Ala | Leu | Thr | Met | Asp | Ser | Lys | Lys |
| | | | | 85 | | | | | 90 | | | | | 95 | |
| Arg | Ile | Gly | Trp | Arg | Phe | Ile | Arg | Ile | Asp | Thr | Ser | Cys | Val | Cys | Thr |
| | | | 100 | | | | | 105 | | | | | 110 | | |
| Leu | Thr | Ile | Lys | Arg | Gly | Arg | | | | | | | | | |
| | | 115 | | | | | | | | | | | | | |

( 2 ) INFORMATION FOR SEQ ID NO:3:

( i ) SEQUENCE CHARACTERISTICS:
( A ) LENGTH: 119 amino acids
( B ) TYPE: amino acid -continued ( C ) STRANDEDNESS: unknown
( D ) TOPOLOGY: unknown ( i i ) MOLECULE TYPE: protein ( x i ) SEQUENCE DESCRIPTION: SEQ ID NO:3:

```
Tyr Ala Glu His Lys Ser His Arg Gly Glu Tyr Ser Val Cys Asp Ser
1               5                   10                  15

Glu Ser Leu Trp Val Thr Asp Lys Ser Ser Ala Ile Asp Ile Arg Gly
            20                  25                  30

His Gln Val Thr Val Leu Gly Glu Ile Lys Thr Gly Asn Ser Pro Val
        35                  40                  45

Lys Gln Tyr Phe Tyr Glu Thr Arg Cys Lys Glu Ala Arg Pro Val Lys
    50                  55                  60

Asn Gly Cys Arg Gly Ile Asp Asp Lys His Trp Asn Ser Gln Cys Lys
65                  70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
            100                 105                 110

Ser Arg Lys Ile Gly Arg Thr
        115
```

MULTIFUNCTIONAL CHIMERIC NEUROTROPHIC FACTORS

This application is a continuation-in-part of U.S. patent application Ser. No. 07/847,369 filed on Mar. 6, 1992 entitled NEUROTROPHIC FACTORS HAVING ALTERED RECEPTOR BINDING SPECIFICITIES, now U.S. Pat. No. 5,344,055.

INTRODUCTION

The present invention provides neurotrophic factors that display multiple neurotrophic specificities. It is based, in part, on the development of a model which enables a determination of the effect of specific residues in neurotrophin molecules on receptor binding, receptor activation and the transduction into a biological response.

BACKGROUND OF THE INVENTION

Many polypeptide growth factors mediate their biological responses by binding to and activating cell surface receptors with intrinsic tyrosine kinase activity. Upon ligand binding, these receptors become autophosphorylated on multiple tyrosine residues and subsequently associate with intracellular molecules important for signal transduction (Ullrich, 1990). However, little is known about the structural determinants of the specificity of ligand-receptor binding and how this interaction results in receptor activation and in the transduction of pleiotropic biological effects.

Recent work on the Trk family of tyrosine kinase receptors has established that these molecules constitute signal-transducing receptors for a family of structurally and functionally related neurotrophic factors collectively known as the neurotrophins. Most of our knowledge on neurotrophic factors comes from work on nerve growth factor (NGF), a 118 amino acid polypeptide that controls the maturation and survival of sympathetic neurons, as well as subpopulations of sensory and central neurons (Levi-Montalcini, 1968; Thoenen, 1980; Thoenen, 1987.) Other neurotrophins include brain-derived neurotrophic factor (BDNF) (Barde 1982; Leibrock, 1989); neurotrophin-3 (NT-3); (Hohn, 1990; Maisonpierre, 1990; Ernfors, 1990; Rosenthal, 1990); and neurotrophin-4 (NT-4); (Hallbook, 1991; Ip, 1992) also named neurotrophin-5 (NT-5); (Berkemeier, 1991). The ability of neurotrophins to promote survival of peripheral and central neurons during development and after neuronal damage has stimulated the interest in these molecules as potential therapeutic agents for the treatment of neurodegenerative diseases and nervous system injuries.

The neurotrophins show about 50% sequence identities and display both overlapping and specific sets of neurotrophic activities on peripheral and central neurons. For example, all neurotrophins, in various proportions, support the survival of neural crest-derived sensory neurons [Thoenen, 1980; Lindsay, 1985; Hohn, 1990; Ip, 1992]. In contrast, survival of embryonic sympathetic neurons is supported only by NGF, while placode-derived sensory neurons are supported by BDNF and NT-3, but not by NGF [Thoenen, 1980; Lindsay, 1985; Hohn, 1990]. This specificity is believed to be achieved in part by the selective interaction between the different neurotrophins and the members of the Trk family of tyrosine kinase receptors expressed on the surface of distinct neuronal populations. Thus, whereas NGF binds only to $p140^{trk}$ (herein called TrkA) [Kaplan, 1991; Kaplan 1991a, Klein, 1991] BDNF and NT-4 interact exclusively with $p145^{trkB}$ (herein called TrkB) [Soppet, 1991; Squinto, 1991; Klein, 1991b; Ip, 1992], while NT-3 interacts with $p145^{trkC}$ (herein called TrkC) and to a lesser extent, also with TrkA and TrkB. [Cordon-Cardo, 1991; Lambelle, 1991; Klein, 1991b; Squinto, 1991].

Unlike Trk receptors, the low-affinity nerve growth factor receptor $p75^{NGFR}$ (herein called LNGFR) [Radeke, 1987; Johnson, 1986] recognizes each of the neurotrophins with a similar affinity [Rodriquez-Tebar, 1990; Ernfors, 1990; Hallbook, 1991; Rodriquez-Tebar, 1992]. Although LNGFR was initially postulated as a component of functional high-affinity NGF receptors (Hempstead, 1989; Hempstead, 1989] involved in mediating biological activity [Hempstead, 1989; Yan, 1991], emerging evidence disputes the direct role of this molecule in signal transduction [Westcamp, 1991, Glass, 1991; Ibáẽez, 1992; Jing, 1992].

Information on neurotrophin-receptor interactions has been obtained from studies of structure-function relationships and the design of neurotrophin mutants with altered properties. For example, in copending parent application Ser. No. 07/847,369 now U.S. Pat. No. 5,349,055 filed on Mar. 6, 1992 entitled NEUROTROPHIC FACTORS HAVING ALTERED RECEPTOR BINDING SPECIFICITIES, which is incorporated by reference in its entirety herein, this approach was used to show that a positively charged interface in the NGF protein formed by Lys-32, Lys-34 and Lys-95 mediates the binding of NGF to LNGFR. NGF molecules mutated in these positions do not bind to LNGFR but retain binding to TrkA receptors and biological activity in cultures of primary neurons, thus demonstrating that TrkA alone is sufficient to mediate the biological activity of NGF in neuronal cells.

Most of the sequence variations among the neurotrophins occur in distinct regions, and initial studies using chimeric molecules between NGF and BDNF have shown that specific combinations of some of these variable sequences allow a broader spectrum of neurotrophic activities than those of the two wild type proteins (Ibáñez, 1991; Surer, 1992). However, these studies did not identify specific receptor binding sites in the neurotrophins responsible for the observed differences in biological specificities.

The recent elucidation of the crystal structure of NGF has localized three quarters of the variable residues in three β-hairpin loops and a reverse turn (McDonald, 1991). Other variable regions include part of a β-strand and the amino ($NH_2$) and carboxy (COOH) termini. The fact that most of the conserved amino acid residues in the neurotrophins play structural roles suggests that all four neurotrophins have very similar conformations, with individual differences restricted to the variable regions (McDonald, 1991). Surface loop regions are in general thought to be important for receptor binding of growth factors (Sclunegger, 1992; Daopin, 1992; Oefner, 1992). For example, in U.S. Pat. No. 5,134,121 issued on Jul. 28, 1992, agonists and antagonists of nerve growth factor are described which consist of peptides derived from the region between amino acid 26 and amino acid 40 of NGF.

SUMMARY OF THE INVENTION

The present invention provides a method for designing potent neurotrophin agonists and antagonists. It is based, in part, on a model developed through the identification of structural elements in the neurotrophins which are responsible for the specificity and activation of Trk receptors. The model described herein is used to design a multifunctional neurotrophin agonist that efficiently activates TrkA, TrkB and TrkC and which displays the neurotrophic specificities of NGF, BDNF and NT-3.

The present invention also provides for nucleic acids encoding altered or mutated or novel neurotrophic factors, for methods of expressing these chimeric neurotrophic factors, for chimeric neurotrophic factor proteins, and for methods of diagnosis and treatment of neurological disorders which utilize the chimeric neurotrophic factors of the invention.

The chimeric neurotrophic factors of the invention provide the activity of several neurotrophic factors in the same molecule. In addition, they may be engineered to be more specific to particular subsets of cells, thus decreasing side-effects caused by nonspecific interactions of the parental molecules.

DETAILED DESCRIPTION OF THE INVENTION

The present invention provides for agonists and antagonists of neurotrophic factors which are members of the neurotrophin family. It is based, in part, on the development of a model which enables the design of molecules that contain specific regions that mimic the receptor binding, and/or receptor activating domains of the neurotrophins.

In accordance with the invention, and as described in detail in the Examples, variable regions from factors, such as neurotrophins, are replaced with corresponding regions from other factors which have comparable three dimensional structure and receptor binding domains. In a preferred embodiment, neurotrophins having novel activity are prepared by exchanging variable portions from corresponding regions in neurotrophins of the same family.

Figure 1B:
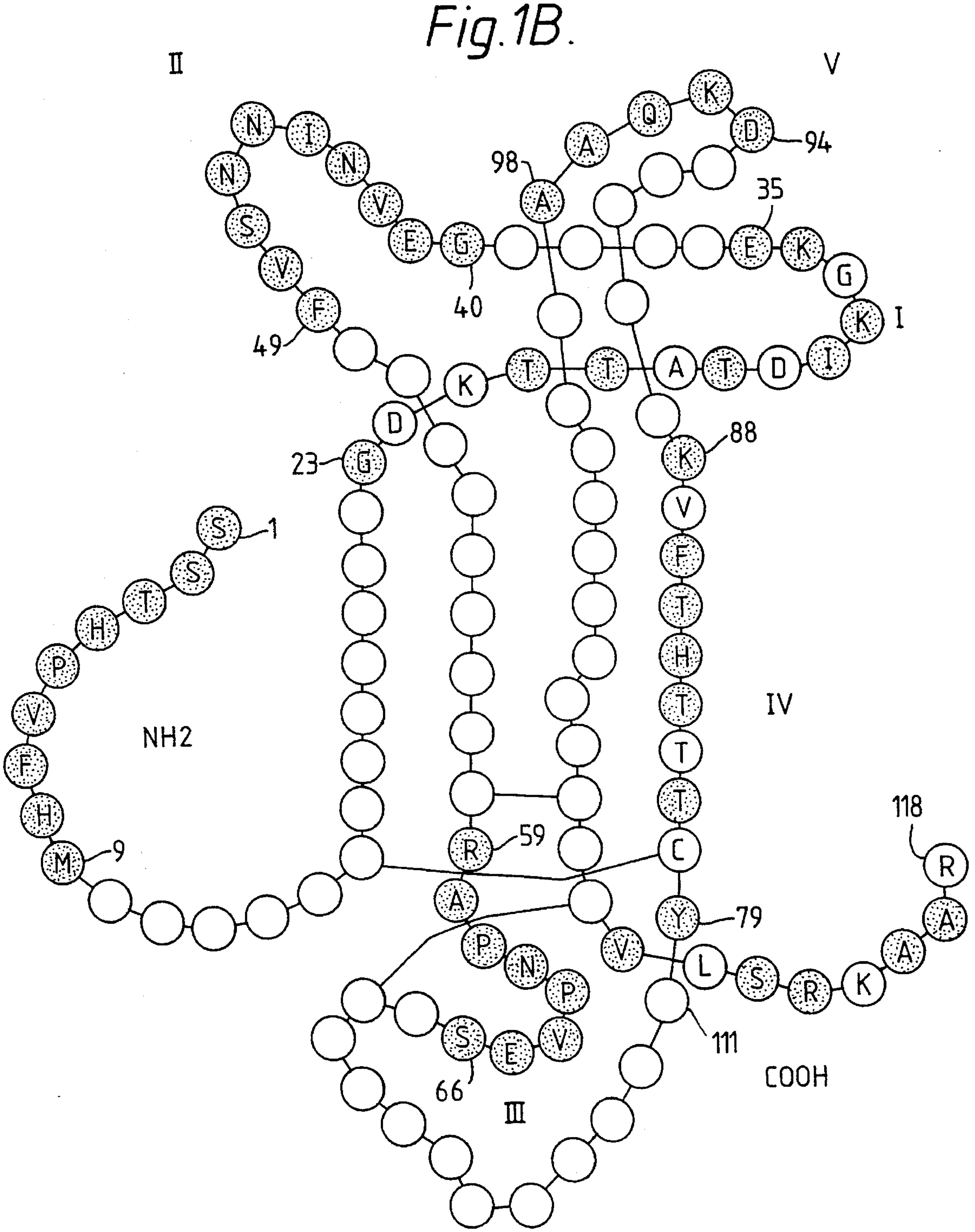
FIG. 1A&B. Variable regions in the neurotrophins. (A) Alignment of the amino acid sequences (single-letter code) of rat NGF (SEQ. ID. NO.1) ([Whittemore, 1988), rat BDNF (SEQ. ID. NO.2) ([Maisonpierre, 1990]) and rat NT-3 (SEQ. ID. NO. 3) ([Ernfors, 1990). Variable regions are boxed and labeled. (B) Schematic representation of the three dimensional structure of the NGF monomer ([McDonald, 1991]). Residues in the different variable regions are indicated by their one-letter code. Residues changed in the NGF protein as a result of the replacement of variable regions from BDNF are shaded. Thick lines at the bottom indicate disulphide bridges.

For example, the nerve growth factor (NGF) family of neurotrophins includes NGF, brain derived neurotrophic factor (BDNF), neurotrophin-3 (NT-3) and neurotrophin-4 (NT-4). FIG. 1A sets forth the alignment of the amino acid sequences (single-letter code) of rat NGF (SEQ. ID. NO. 1) ([Whittemore, 1988), rat BDNF (SEQ. ID. NO. 2) ([Maisonpierre, 1990]) and rat NT-3 (SEQ. ID. NO. 3) ([Ernfors, 1990). Variable regions are boxed and labeled.

According to the invention, variable regions from each of the neurotrophins are replaced with corresponding regions from other members of the family and the resulting chimeras tested for the gain or loss of specific functions associated with each of the parental factors. Such functions include, but are not limited to 1) ability to bind the relevant receptor, e.g. TrkA, TrkB or TrkC; 2) phosphorylation of the relevant receptor; 3) induction of immediate early genes; and 4) biological activity.

Thus, for example, in one embodiment, variable region V from NT-3 (amino acids 94–98) is replaced with the corresponding region from BDNF. (The resultant construct would be designated BDNF V/NT-3 to indicate the source of the variable region substituted into the NT-3 molecule). The resultant construct was found to have enhanced ability to bind TrkB and enhanced ability to support the survival of nodose ganglion neurons as compared to the parental NT-3 molecule.

Based on the functional information obtained with chimeric and mutant molecules, a chimeric neurotrophin was constructed that displays biochemical and biological properties from three different neurotrophins. In this construct, variable region (see SEQ. ID. NO. 3) V of NT-3 was replaced with the corresponding amino acids from BDNF (see SEQ. ID. NO. 2), and the amino terminus region of the NT-3 (residues 3–9:SEQ. ID. NO. 3) was replaced with the corresponding region from NGF (see SEQ. ID. NO. 1). The resultant factor, designated pan neurotrophin-1 (PNT-1) efficiently activated TrkA, B and C receptors and displayed biological specificities on neurons characteristic of NGF, BDNF and NT-3. This result demonstrates that the structural-functional information obtained can be used for engineering of molecules with broader or novel biological specificities.

The present invention provides for the use of chimeric neurotrophic factors which offer the advantage of providing the activities typically associated with several neurotrophic factors. Such factors can be used to promote the growth and/or survival of cells of the nervous system, in particular, but not limited to, dopaminergic neurons, cholinergic neurons, sensory neurons, striatal cells, cells of the cortex, striatum, hippocampus, cerebellum, olfactory bulbs, periaqueductal gray, raphe nucle, locus coeruleus, dorsal root ganglion, neural placode derivatives, sympathetic neurons and upper and lower motor neurons.

The factors described herein may be particularly useful for the treatment of diseases or disorders which involve damage to both sensory and motor neurons, including, for example, damage caused by chemotherapy or neuropathies such as those associated with diabetes. In the central nervous system, the novel neurotrophins described herein may provide enhanced specificity and improved diffusion characteristics over the parental molecules, thus providing a useful means of treating diseases such as Alzheimers which involve loss of multiple types of neuronal cells.

The chimeric neurotrophic factors produced according to the present invention can be used to treat any disease or disorder for which the individual factors are useful. For example, PNT-1 promotes the survival of both sympathetic ganglia, as well as populations of nodose ganglia, the survival of which have been shown to be supported by parental BDNF and NT-3 factors. Such a factor may prove to be particularly useful to treat diseases or disorders which involve sympathetic, parasympathetic and sensory neurons.

In a specific embodiment of the invention, administration of the factors of the present invention can be used in conjunction with surgical implantation of tissue in the treatment of Alzheimer's disease and/or Parkinson's disease. Factors such a PNT-1 may be used to promote the survival of dopaminergic neurons of the substantia nigra in a dose-dependent manner, supporting the use of the factors in the treatment of disorders of CNS dopaminergic neurons, including, but not limited to, Parkinson's disease. In addition, PNT-1 would be expected to sustain the survival of CNS cholinergic neurons and, in particular, basal forebrain cholinergic neurons, indicating that they may be useful in the treatment of disorders involving cholinergic neurons, including, but not limited to Alzheimer's disease. It has been shown that approximately 35% of patients with Parkinson's disease suffer from Alzheimer-type dementia; factors produced according to the invention may prove to be a useful single agent therapy for this disease complex. Similarly, factors produced according to the invention may be used therapeutically to treat Alzheimer's disease in conjunction with Down's Syndrome.

Effective doses of the factors described herein formulated in suitable pharmacological carriers may be administered by any appropriate route including but not limited to injection (e.g., intravenous, intraperitoneal, intramuscular, subcutaneous, etc.), by absorption through epithelial or mucocutaneous linings (e.g., oral mucosa, rectal and intestinal mucosa, etc.); etc.

In addition, the factors may be used in any suitable pharmacological carrier, linked to a carrier or targeting molecule (e.g., antibody, hormone, growth factor, etc.) and/or incorporated into liposomes, microcapsules, and controlled release preparation prior to administration in vivo.

In addition to chimeric neurotrophic factors, the present invention further contemplates the construction of chimeric growth factors which have characteristics derived from the neurotrophins. For example, specific regions of growth factors having similar structural features to the neurotrophins may be replaced with the corresponding regions from the neurotrophins to provide additional properties to such molecules.

The invention further contemplates the use of rational drug design to construct a protein or non-protein small molecule whose structure mimics the tertiary structure of the NGF molecule described in example 5 and which is capable of interacting with a neurotrophic factor receptor and which functions as an agonist or antagonist of the neurotrophic factor. For example, the fact that chimeric molecules such as I+II+III+IV+V retained high levels of receptor binding but showed low biological activity, reveals a strategy to design neurotrophin antagonists.

EXAMPLES

MATERIALS AND METHODS

The following materials and methods were used for each of the examples below:

DNA cloning and site-directed mutagenesis

Fragments containing the pre-pro-coding sequences from the rat NGF ([Whittemore, 1988]), mouse BDNF ([Hofer, 1990]) and rat NT-3 ([Ernfors, 1990]) genes were cloned into pBS KS+ (Stratagene). Note that the amino acid sequence of mouse and rat BDNF are identical ([Maisonpierre, 1190]). Single stranded DNA from these plasmids was used as template for oligonucleotide based site-directed mutagenesis as described by Kunkel ([Kunkel, 1985]). The replacements were confirmed by nucleotide sequence analysis by the chain-termination method ([Sanger, 1977]). For protein expression, DNA inserts containing the desired replacements were subcloned in pXM ([Yang, 1986]).

Production and a quantitation of recombinant proteins

COS cells grown to about 70% confluency were transfected with 25 μg plasmid DNA per 100 mm dish using the DEAE dextranchloroquine protocol ([Luthman, 1982]). To correct for differences in the amounts of recombinant protein produced by the different constructs, 35 mm dishes transfected in parallel were maintained in the presence of 100 μCi/ml $^{35}$S-cysteine (Amersham). Aliquots of conditioned media were then analyzed by SDS/PAGE and the amounts of recombinant protein in the different samples were equilibrated after densitometer scanning of the corresponding autoradiograms as previously described ([Ibáñez, 1991]). The absolute amount of wt NGF protein was determined by quantitative immunoblotting of conditioned media and by measurement of biological activity in cultured sympathetic ganglia using standards of purified mouse NGF ([Ibáñez, 1991]). The data obtained from these analysis were then used to determine the protein concentration in the samples containing wt BDNF, wt NT-3, chimeric and mutant proteins.

Binding Assays

Purified mouse NGF and BDNF were labeled with $^{125}$I by the lactoperoxidase method to an average specific activity of $1\times10^8$ cpm/μg. For the labeling of BDNF, the modifications described by Rodriguez-Tebar et al. ([Rodriguez-Tebar, 1992]) were used. NIH3T3 fibroblasts expressing TrkA, TrkB or TrkC were used at 2 to $1\text{–}\times10^6$ cells/ml. Steady state binding was measured in competition assays performed at 4° C. using $1.5\times10^{-9}$M $^{125}$I-BDNF and serial dilutions of conditioned media containing equivalent amounts of wt or mutated NGF protein. All components were added at the same time and the cells were collected by centrifugation after equilibrium was reached (90–120 minutes incubation). Cell pellets were then counted in a gamma counter. Control experiments using medium from mock transfected COS cells showed that other proteins present in the conditioned medium had no effect on the binding of $^{125}$I-NGF or $^{125}$I-BDNF to the cells. Nonspecific binding was measured in a parallel incubation to which 300 to 1000-fold molar excess of unlabelled purified factor was added. All results were corrected for this nonspecific binding, which was less than 10% (for NGF) or 30% (for BDNF) of total binding. The concentration of each chimeric, mutant and wild type molecule that gave 50% binding ($IC_{50}$) was determined, and relative binding was calculated using the relationship:(mutant $IC_{50}$/wild type $IC_{50}$)X 100.

Phosphorylation assays

A confluent 10 cm plate containing about $10^7$ rtrk-3T3 or rtrkB-3T3 cells was treated for 5 minutes at 37° C. with wt, chimeric or mutant factors and subsequently lysed with 1 ml of ice-cold buffer containing 1% NP40, 20mM Tris pH 8.0, 137 mM NaCl, 2 mM EDTA, 10% glycerol, 1 mM PMSF, 0.15 U/ml aprotinin, 20 μM leupeptine and 1 mM Na orthovanadate. Plates were incubated 15 minutes at 4° C. after which insoluble material was removed by centrifugation. Cell lysates were normalized for protein content before immunoprecipitation. Trk immunoprecipitation was performed by incubating lysates with 1 μl of anti-TrkB polyclonal antiserum 443 ([Soppet, 1991]) which recognizes TrkA, TrkB and TrkC. After 2 hr at 4° C., immunocomplexes were collected with Protein A-Sepharose (Pharmacia, Sweden), washed in lysis buffer and boiled for 5 minutes before SDS/PAGE. After electrophoresis, gels were blotted to nitrocellulose membranes, reacted with antiphosphotyrosine monoclonal antibody 4G10 (UBI, New York) and developed with the ECL Western Detection System (Amersham, UK). Appropriately exposed autoradiograms of phosphotyrosine blots were used for densitometric scanning.

Biological assays

Serial dilutions of conditioned media containing equivalent amounts of recombinant protein were assayed for stimulation of neurite outgrowth on explanted chick embryonic day 8 (E8) sympathetic and nodose ganglia as previously described ([Ebendal, 1989]; [Ibáñez, 1991]). Fibre outgrowth was scored on a semiquantitative scale in biological units (BU) by comparison to standards obtained with purified mouse NGF, for which 1 BU is equivalent to approximately 5 ng/ml. The concentration of each protein that gave 0.6 BU in this scale was determined, and used to calculate the relative activity compared to that obtained with wt NGF.

Dissociated neurons from chick E8 sympathetic and nodose ganglia were preplated on plastic for 2 hr and then cultured in 96 well-plates coated with poly-L-ornithine and laminin at a density of 800–1000 cells/well. Serial dilutions of conditioned media containing equivalent amounts of recombinant proteins were added at the time of plating and neuronal survival was determined after 36–48 hr by phase contrast microscopy, scoring the number of surviving neurons in the entire well.

Figure 2A:
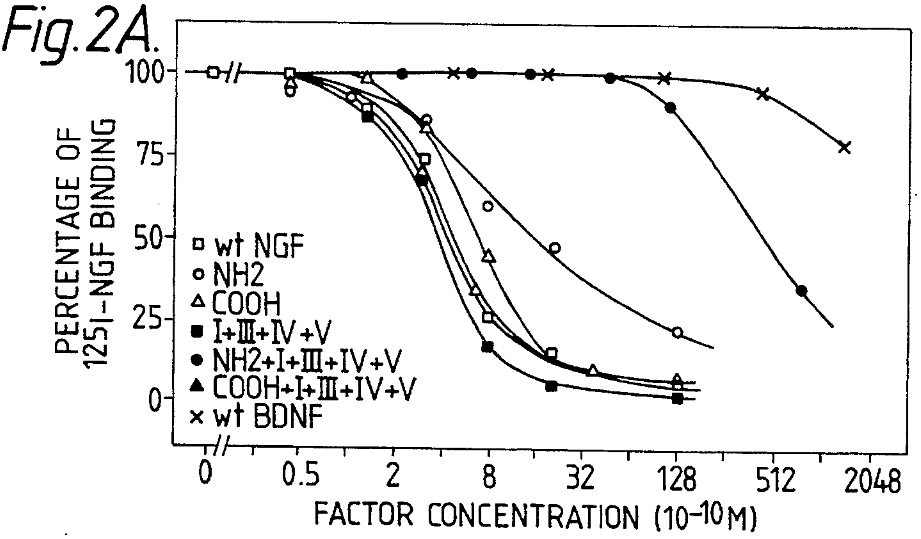
FIG. 2A–D. TrkA receptor binding, receptor phosphorylation and biological activity of wild-type (wt) and chimeric molecules (see SEQ. ID. NOS. 1 and 2 for all chimeric constructions. (A) Serial dilutions of transfected COS cell conditioned medium containing equal amounts of wt NGF (□), wt BDNF (*) and chimeric molecules $NH_2$ (○), COOH (Δ), I+III+IV+V (■), $NH_2$+I+III+IV+V (●) and COOH+I+III+IV+V (▲) were assayed for their ability to displace $^{1254}$I-NGF from these cells. Each point represents the mean of triplicate determinations. Standard deviation was at or generally below ±10%. (B) and (C) Tyrosine phosphorylation of TrkA receptors stimulated by wt NGF, wt BDNF and chimeric molecules. rtrkA-3T3 cells were treated with 100 ng/ml of the indicated recombinant proteins and assayed for tyrosine phosphorylation. Media from mock-transfected COS cells was used as negative control (CONTROL). Arrowhead indicates the migration of phosphorylated TrkA (p140$^{trk}$). The faster migrating band correspond to constituitively phosphorylated p140$^{trk}$ precursors ([Kaplan, 1991] ). (D) Serial dilutions of transfected COS cell conditioned medium containing equal amounts of wt and chimeric factors were assayed for their ability to stimulate neurite outgrowth from E8 chick sympathetic ganglia. Data from three determinations varied by ±20% of the average values reported here. Key symbols as in (A).
Figure 2B:
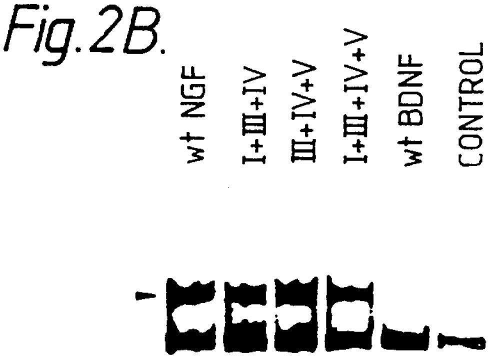
Figure 2C:
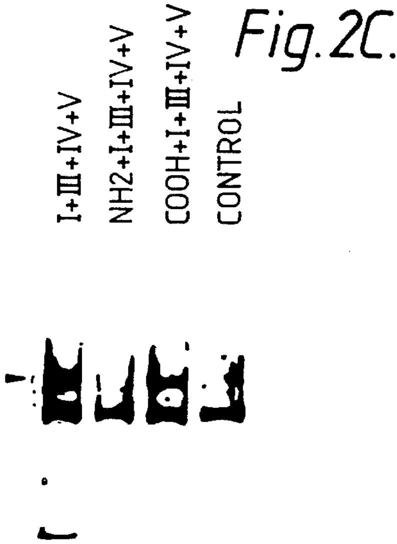
Figure 2D:
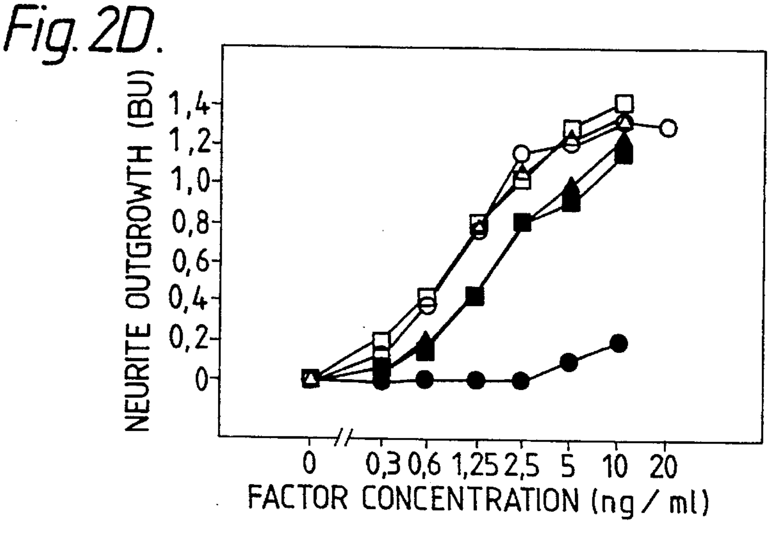

EXAMPLE 1. Structural elements in. NGF responsible for binding to and activation of TrkA Previous studies have shown that NGF can tolerate considerable structural changes without substantial loss of biological activity (Ibáñez, 1990; Ibáñez, 1991, Ibáñez, 1992). Consistent with this observation, the individual replacement of variable regions I, II, III, IV or V with the comparable regions from BDNF generated chimeric molecules that were indistinguishable from wt NGF in TrkA receptor binding, activation and in their biological activity (not shown) (see SEQ. ID. NOS. 1 and 2 for all chimera construction). Moreover, the chimeric molecule I+III+IV+V retained wild-type levels of binding to TrkA in spite of having more than 50% of its variable sequences replaced by the corresponding sequences from BDNF (FIG. 2A and Table 1). Replacement of these regions did not affect the level of TrkA tyrosine kinase phosphorylation (FIG. 2B) but it reduced biological activity on sympathetic neurons to 50% of wild-type NGF (FIG. 2D and Table 1). These results suggested that the remaining NGF variable regions (i.e. region II and $NH_2$ and COOH termini) could be responsible for the NGF activities of the I+III+IV+V molecule. To test this, the $NH_2$ and COOH-termini in wild-type NGF and in the I+III+IV+V chimera were replaced by those of BDNF. Replacement of the COOH terminus of NGF with that of BDNF had no effect on TrkA binding, TrkA activation or biological activity (FIGS. 2A, C, D and Table 1). However, replacement of the $NH_2$ terminus reduced the affinity of binding to TrkA 4 to 5-fold (FIG. 2A). Interestingly, neither TrkA phosphorylation nor biological activity were affected by the reduced TrkA binding (Table 1 and FIG. 2D). However, replacement of the $NH_2$ terminus in the I+III+IV+V chimera reduced binding, receptor phosphorylation and biological activity to less than 1% of wild type NGF (FIGS. 2A, C and D). Note that this chimera retained the two $NH_2$-terminal Ser residues from NGF followed by the $NH_2$-terminus from BDNF (FIG. 1A). Additional molecules were therefore constructed with the $NH_2$-terminus (not shown), indicating that residues important for TrkA binding in this region are located between positions 3 and 9.

The differences observed between the $NH_2$, I+III+IV+V and $NH_2$+I+III+IV+V molecules suggested that apart from the $NH_2$-terminus, other variable regions could cooperate synergistically with the $NH_2$-terminus to promote binding, receptor activation and biological activity. To test this possibility, we alternately changed back variable regions I, IV or V in the $NH_2$+I+III+IV+V chimera to those of NGF, thereby generating molecules $NH_2$+III+IV+V, $NH_2$+I+III+V and $NH_2$+I+III+IV, respectively.

Figure 3A:
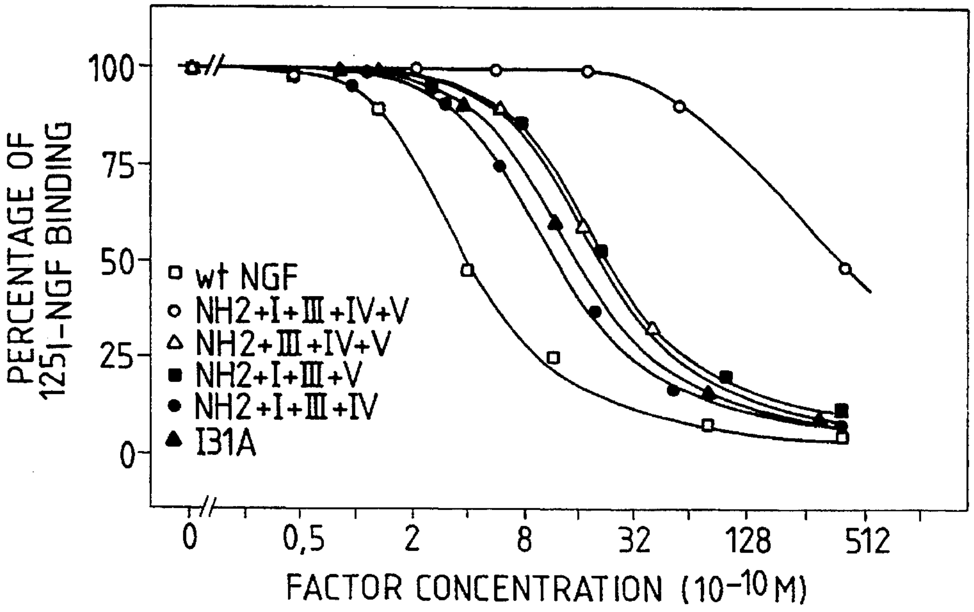
FIG. 3A&B. NGF variable regions I, IV and V partially restore TrkA binding and biological activity of the $NH_2$+I+III+IV+V chimeric molecule (see SEQ. ID. NOS. 1 and 2 for all chimera construction). (A) Serial dilutions of transfected COS cell conditioned medium containing equal amounts of wt NGF (□), chimeric molecules $NH_2$+I+III+IV+V (○), $NH_2$+III+IV+V (Δ), $NH_2$+I+III+V (■), $NH_2$+I+III+IV (●) and NGF mutant 131A (Δ) were assayed for their ability to displace $^{125}$I-NGF from receptors on rtrkA-3T3 cells. Medium from mock-transfected cells failed to displace $^{125}$I-NGF from these cells. Each point represents the mean of triplicate determinations. Standard deviation was at or generally below ±10%. (B) Serial dilutions of transfected COS cell conditioned medium containing equal amounts of wt, mutant and chimeric factors were assayed for their ability to stimulate neurite outgrowth from E8 chick sympathetic ganglia. Data from three determinations varied by ±20% of the average values reported here. Key symbols as in (A).
Figure 3B:
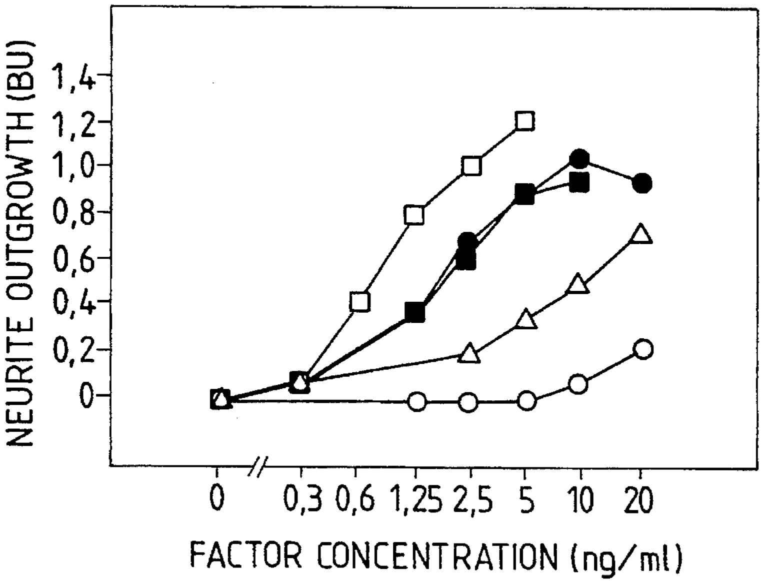

Any of these three changes partially restored receptor binding (FIG. 3A and Table 1), supporting the argument that regions I, IV and V are also involved in contact to TrkA. More receptor binding was rescued by region V (chimera $NH_2$+I+III+IV) than by regions I or IV (chimeras $NH_2$+III+IV+V or $NH_2$+I+III+V, respectively), although none of these changes resulted in more than 20–25% of wild-type NGF binding (Table 1). Receptor phosphorylation and biological activity in sympathetic neurons were restored to 40% of wild type NGF (FIG. 3B and Table 1). In the biological assay, chimeras $NH_2$+I+III+V and $NH_2$+I+III+IV were more effective than $NH_2$+III+IV+V, indicating that regions IV and V can rescue NGF responsiveness more efficiently than region I (Table 1). Previous results from alanine scanning of variable region I suggested that Ile-31 is important for maximal NGF biological activity (Ibáñez, 1992). In agreement with this, Ala-replacement of Ile-31 resulted in a 4-fold reduction in TrkA receptor binding (FIG. 3B), indicating that this exposed hydrophobic residue is involved in the contact to TrkA.

Figure 4A:
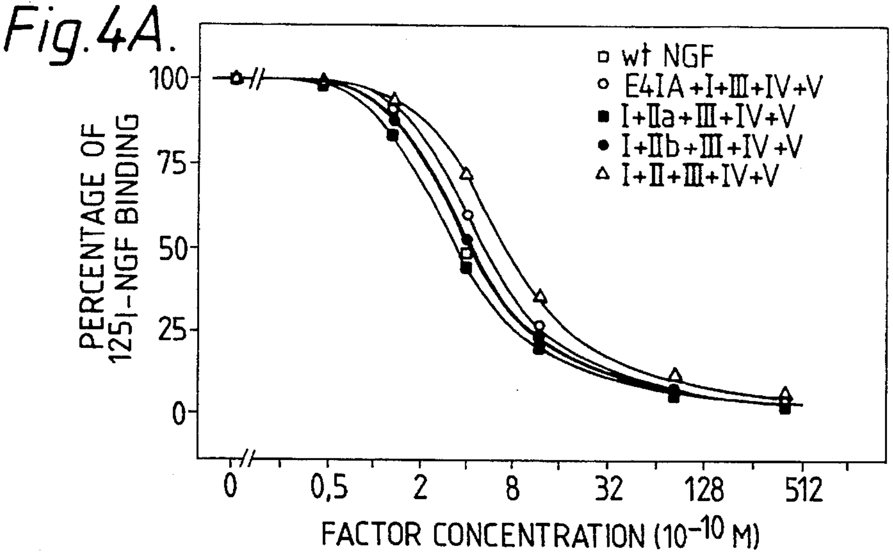
FIG. 4A–D Residues in variable region II of NGF are involved in TrkA activation and bioactivity but not in TrkA binding (see SEQ. ID. NOS. 1 and 2for all chimera constructions). (A) Serial dilutions of transfected COS cell conditioned medium containing equal amounts of wt NGF (□) and chimeric molecules E41A+I+III+IV+V (○), I+IIa+III+IV+V (■), I+IIb+III+IV+V (●) and I+II+III+IV+V (▲) were assayed for their ability to displace $^{125}$I-NGF from these cells. Each point represents the mean of triplicate determinations. Standard deviation was at or generally below ±10%. (B) and (C) Tyrosine phosphorylation of TrkA receptors stimulated by wt NGF and chimeric molecules. rtrkA-3T3 cells were treated with 100 ng/ml of the indicated recombinant proteins and assayed for tyrosine phosphorylation. Arrowhead indicates the migration of phosphorylated TrkA (p140$^{trk}$). The faster migrating band correspond to constituitively phosphorylated p140$^{trk}$ precursors (Kaplan, 1991). (D) Serial dilutions of transfected COS cell conditioned medium containing equal amounts of wt and chimeric factors were assayed for their ability to stimulate neurite outgrowth from E8 chick sympathetic ganglia. Data from three determinations varied by ±20% of the average values reported here. Key symbols are as in (A) except for chimeric molecule I+III+IV+V (Δ).
Figure 4B:
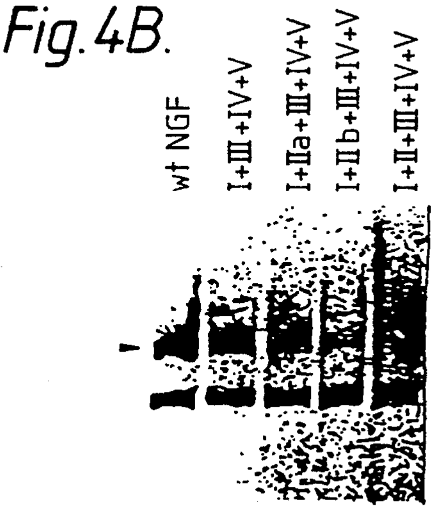

Replacement of regions IIa, IIb and IIa+IIb (i.e. region II) in wild-type NGF reduced the amount of recombinant protein to almost undetectable levels. However, replacement of these regions in the I+III+IV+V chimera allowed production of protein at 5 to 10% of wild-type levels. Chimeric molecules containing these variable sequences from BDNF still retained high levels of binding to TrkA (FIG. 4A and Table 1). Moreover, chimeric molecule I+IIa+III+IV+V was indistinguishable from I+III+IV+V in receptor phosphorylation and biological activity on neurons (FIG. 4B and D). In contrast, a drastic decrease in both receptor activation and biological activity was observed when residues 45 to 49 were replaced (chimeric molecule I+IIb+III+IV+V) (FIGS. 4B, D and Table 1), indicating that the second half of this variable loop is important for activation of the TrkA receptor by NGF. Replacement of the complete region II (molecule I+II+III+IV+V) resulted in even lower levels of receptor phosphorylation and bioactivity (FIGS. 4B, D and Table 1). Interestingly, despite their low biological activity, these two molecules maintained high levels of TrkA binding, probably due to the fact that they retain the $NH_2$ terminus from NGF.

Figure 4C:
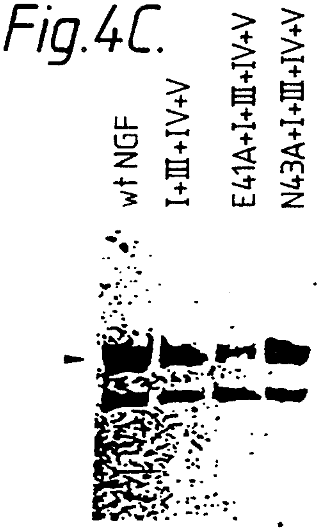
Figure 4D:
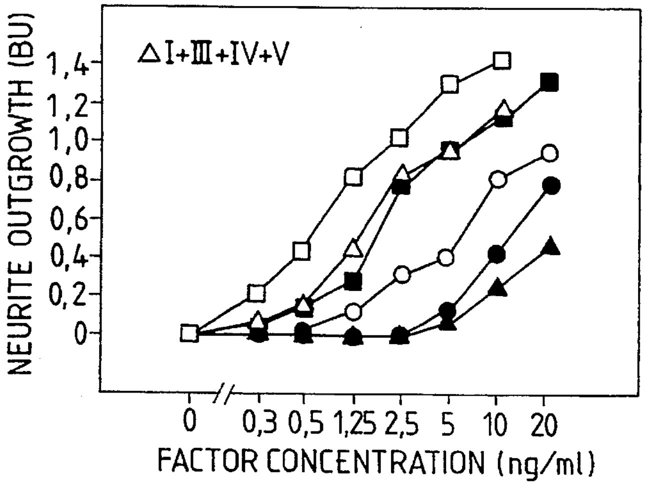

The functional importance of amino acid residues in variable region II was further investigated by alanine-scanning mutagenesis. Glu-41, Asn-43, Ile-44, Asn-45, Asn-46 and Val-48 were individually replaced by Ala in wild-type NGF. Surprisingly, none of these mutations affected receptor binding, receptor phosphorylation or bioactivity of the NGF molecule. The same alanine-scaning mutagenesis was then performed in the I+III+IV+V molecule. This chimera provided a more sensitive background where the effect of individual changes was more evident. In this context, replacement of Glu-41 by Ala substantially reduced TrkA phosphorylation and biological activity (FIGS. 4C, D and Table 1). Mutation of Asn-45 showed a less pronounced effect, while Ala-replacement of any of the other positions had no effect (Table 1).

Figure 5A:
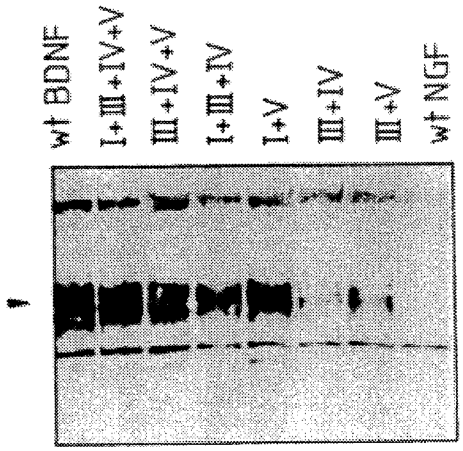
FIGS. 5A–E. TrkB receptor binding, receptor phosphorylation and biological activity of wt and chimeric molecules (see SEQ. ID. NOS. 1 and 2 for all chimera constructions) . (A)(B) and (C) Tyrosine phosphorylation of TrkB receptors stimulated by wt NGF, wt BDNF and NGF mutant chimeric molecules. rtrkB-3T3 cells were treated with 100 ng/ml of the indicated recombinant proteins and assayed for tyrosine phosphorylation. Arrowhead indicates the migration of phosphorylated TrkB (p 145$^{trkB}$). (D) Serial dilutions of transfected COS cell conditioned medium containing equal amounts of wt BDNF (□), wt NGF (●) and chimeric molecules I+III+IV (○), III+IV+V (Δ) and I+III+IV+V (■) were assayed for their ability to displace $^{125}$I-BDNF from receptors on rtrkB-3T3 cells. Medium from mock-transfected cells failed to displace $^{125}$I-BDNF from these cells. Each point represents the mean of triplicate determinations. Standard deviation was at or generally below ±10%. (E) Neuronal survival of dissociated E8 chick neurons from the nodose ganglion in the presence of saturating amounts (20–50 ng/ml) of wt BDNF, wt NGF and chimeric molecules. Media from mock-transfected COS cells was used as a negative control (control). Results are presented as the mean of triplicate determinations ±SD.
Figure 5B:
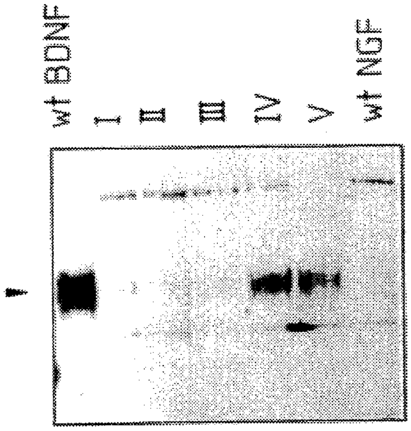

EXAMPLE 2. Structural elements in BDNF responsible for binding to and activation of Trk B Chimeric molecules with some combinations of variable regions I, III, IV and V have previously been shown to display neurotrophic specificities characteristic of both NGF and BDNF, since they stimulated neurite outgrowth from both sympathetic and nodose ganglia (Ibáñez, 1991). In agreement with those observations, chimeric molecules III+IV+V and I+III+IV+V stimulated high levels of tyrosine phosphorylation of TrkB receptors (FIG. 5A). Chimeric molecule I+III+IV and the double chimeras I+V and III+IV also stimulated TrkB phosphorylation (FIG. 5A) despite the fact that no BDNF-like biological activities were seen with these molecules (Ibáñez, 1991). The receptor phosphorylation assay therefore detected ligand-receptor interactions that were presumably too weak to trigger a biological response (see below). In assays of chimeric molecules with individual replacements of variable sequences no TrkB activation was seen with regions II, III or the $NH_2$- and COOH-termini (FIGS. 5B and 5C and Table 2), although in the case of region II, this could be due to the low level of production of this chimeric molecule. In contrast, significant receptor phosphorylation was detected with chimeric molecules IV and V and a weak but consistent signal was detected with chimera I (FIG. 5B), suggesting that these regions interact with the TrkB receptor. Note that the same regions were also found to be involved in the contact of NGF with TrkA (FIGS. 3A and 3B).

Figure 5C:
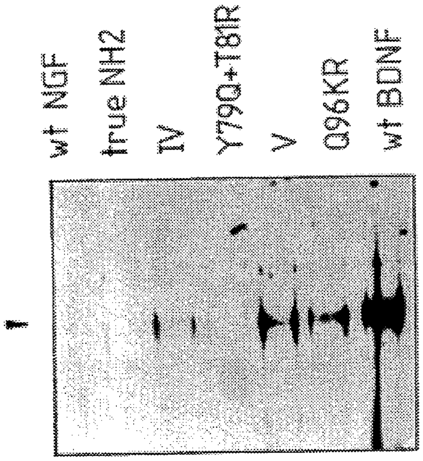

Three main changes were introduced in NGF after replacement with BDNF variable region IV: Tyr-79, Thyr-81, and His-84 by Gln, Arg and Gln, respectively. (FIG. 1A). Interestingly, these residues are also present in other neurotrophins reported to interact with TrkB, i.e. NT-3 and NT-4. On the other hand, in variable region V, BDNF has three positively charged residues in positions 95, 96 and 97 which are not present in the other neurotrophins. We therefore investigated the possibility that some of these residues could be responsible for the ability of chimera IV and V to activate the TrkB receptor. Tyr-79 and Thr-81 in region IV, were simultaneously replaced by Gln and Arg, respectively, and Gln-96, in region V, was replaced by the dipeptide Lys-Arg. The double mutant Y79Q+T81R failed to stimulate TrkB phosphorylation at the level seen with region IV (FIG. 5C), indicating that Gln at position 84 is important, and/or that synergistic cooperation of these three residues is necessary for receptor activation. In contrast, mutation of Gln-96 in NG into Lys-Arg resulted in a molecule able to stimulate tyrosine phosphorylation of TrkB (FIG. 5C). This mutant caused the same level of receptor activation as chimera V, suggesting that the positive charges in region V are important for activation of TrkB. Comparison of the results illustrated in FIG. 5A, 5B and 5C indicates that the effects of replacements and mutations on receptor activation are only partially additive, suggesting that both independent and synergistic contacts are being made with the receptor.

Figure 5D:
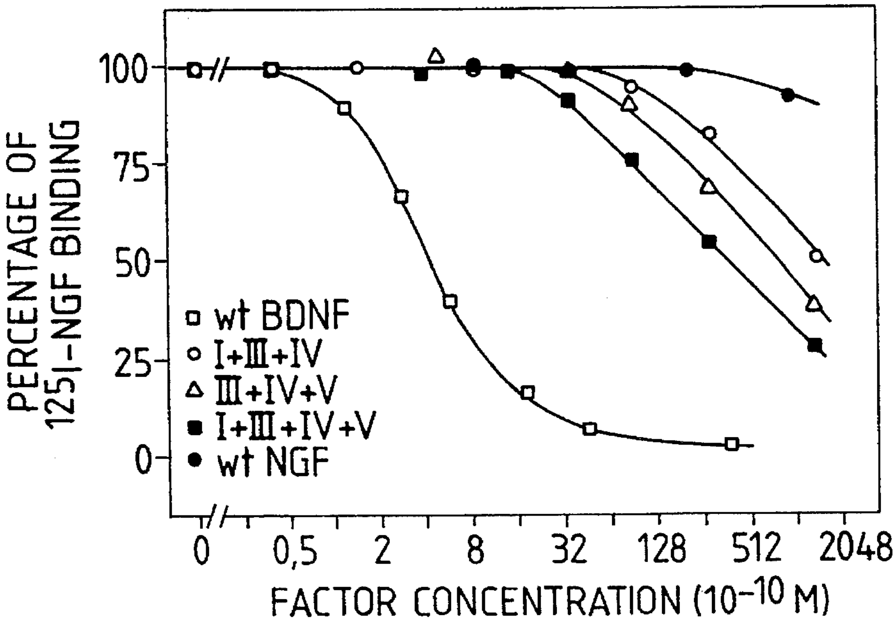
Figure 5E:
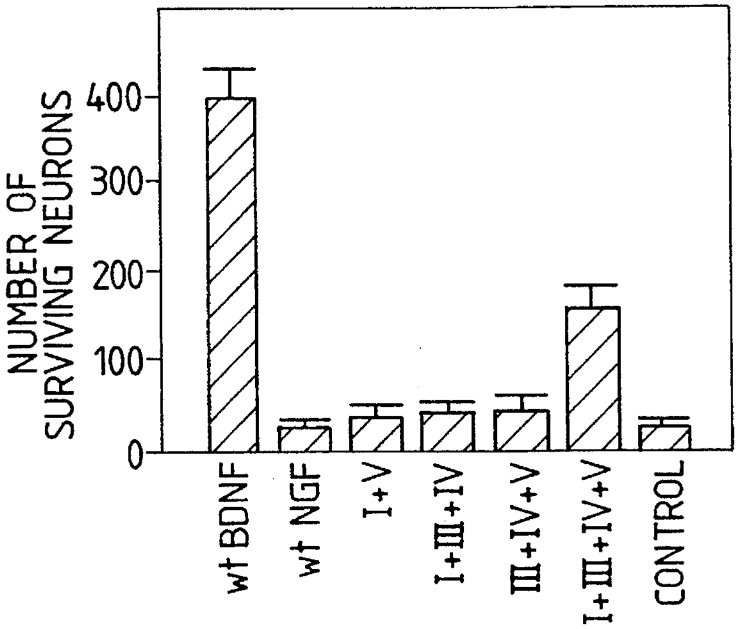

Despite their ability to stimulate TrkB phosphorylation, these molecules showed very low levels of receptor binding in competitive binding assays. As illustrated in FIG. 5D, molecules chimeric at multiple regions (including chimera I+III+IV+V) showed binding affinities that were 100 to 300 fold lower than wild-type BDNF (FIG. 5D and Table 2). In order to investigate to what extent the receptor phosphorylation observed with these molecules translates into a biological effect, the ability of different chimeras to promote survival of dissociated neurons from the nodose ganglion was assayed. From all of the combinations of variable regions I, III, IV and V tested, only chimeric molecule I+III+IV+V promoted the survival of nodose neurons. However, only 30% of the neurons could be rescued with saturating amounts of this protein compared to wild-type BDNF (Table 2 and FIG. 5E). Other chimeric molecules failed to promote survival of neurons from the nodose ganglion, even though previous studies indicated that some of them (i.e. chimeric molecules III+V and Ill+IV+V) are able to induce neurite outgrowth from explants of this ganglion (Ibáñez, 1991) (see below).

Figure 6A:
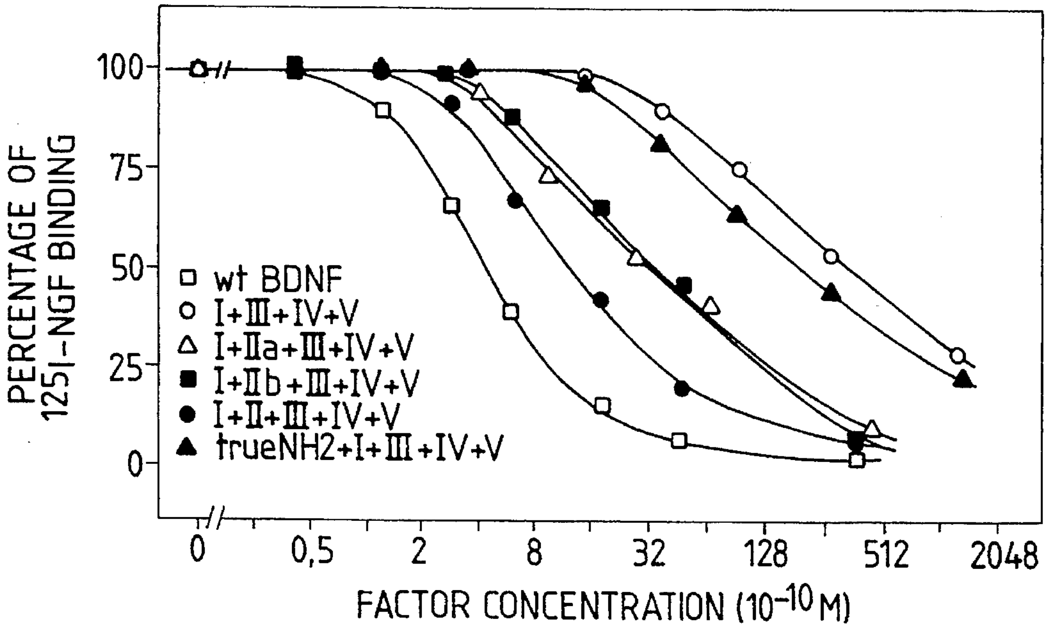
FIGS. 6A&B. Residues in variable region II of BDNF confer TrkB binding and BDNF-like biological activity to chimeric molecules (see SEQ. ID. NOS. 1 and 2 all chimera constructions). (A) Serial dilutions of transfected COS cell conditioned medium containing equal amounts of wt BDNF (□) and chimeric molecules I+III+IV+V (○), I+IIa+IV+V (Δ), I+IIb+III+IV+V (■), I+11+III+IV+V (●) and true$NH_2$+I+III+IV+V (▲) were assayed for their ability to displace $^{125}$I-BDNF from receptors on rtrkB-3T3 cells. Medium from mock-transfected cells failed to displace $^{125}$I-BDNF from these cells. Each point represents the mean of triplicate determinations. Standard deviation was at or generally below ±10%. (B) Neuronal survival of dissociated E8 chick nodose neurons in the presence of saturating amounts (20–50 ng/ml) of wt BDNF and chimeric molecules. Media from mock-transfected COS cells was used as negative control (control). Results are presented as the mean of triplicate determinations ±SD.

The low receptor binding displayed by molecule I+III+IV+V prompted an investigation of the contribution of variable region II and the $NH_2$ and the COOH termini of BDNF to TrkB binding. In contrast to what was seen for NGF, replacement with the $NH_2$-terminus of BDNF into the I+III+IV+V chimera produced only a minor improvement in binding to TrkB (Table 2 and FIG. 6A). Replacement of sequences from variable region II resulted in chimeric molecules with increased affinity for TrkB receptors (FIG. 6A and Table 2). Both halves of variable region II were equally effective in improving binding to TrkB now reaching 12% of the level seen with wild-type BDNF (Table 2). The two sequences cooperated synergistically since the I+II+III+IV+V molecule bound to TrkB with only 2-fold lower affinity than wild type BDNF (FIG. 6A and Table 2).

Figure 6B:
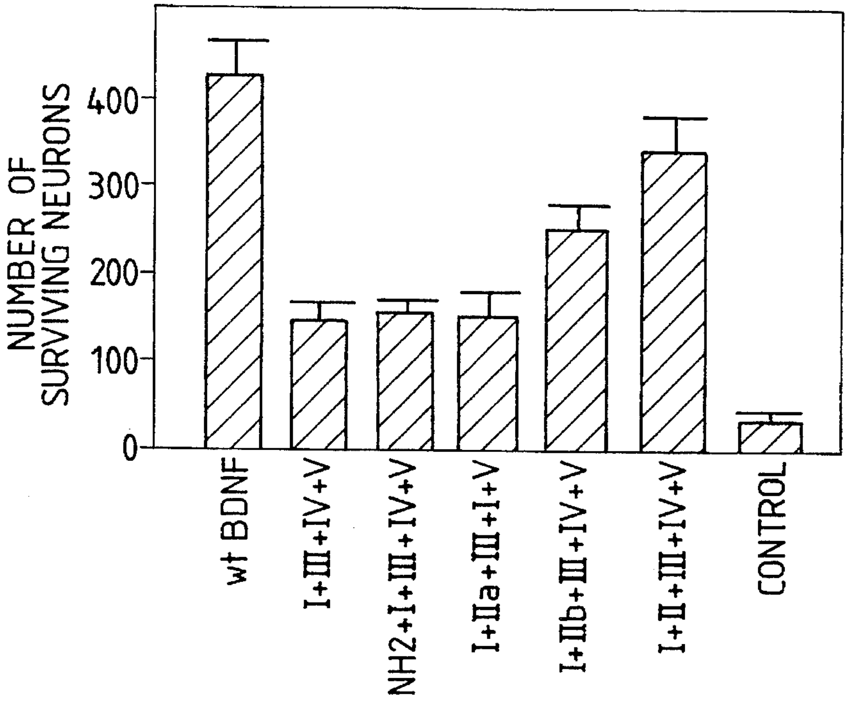

Replacement of sequences from the $NH_2$ and COOH termini of BDNF in the I+III+IV+V molecule did not improve biological activity on nodose neurons (FIG. 6B) However, replacement of region IIb, but not IIa, resulted in a molecule able to rescue 60% of the nodose neurons compared to wild type BDNF (FIG. 6B and Table 2). This indicates that residues 45–49 in BDNF are important for further activation of the TrkB receptor. Note that this region, but not region IIa, was also found to be important for TrkA activation by NGF (FIG. 4B). Biological activity in nodose neurons reached 80% of wild type BDNF levels when the complete region II was replaced (residues 40–49) (FIG. 6B and Table 2) suggesting that region IIa (residues 40–44) contributes indirectly by allowing a conformation of this loop that facilitates the contact of residues 45–49 with the TrkB receptor.

EXAMPLE 3. Similar levels of TrkB receptor phosphorylation may result indifferent biological properties As shown in FIG. 5, several chimeric molecules caused a substantial phosphorylation of TrkB receptors but failed to elicit BDNF-like biological activities in neurons. Moreover, an intriguing discrepancy was seen between the abilities of some chimeric molecules (i.e. Ill+IV+V) to promote neurite outgrowth and neuronal survival. The possible significance of these differences was explored by comparing the dose-response of TrkB phosphorylation and biological activities between some of these chimeric molecules and wild-type BDNF.

Figure 7A:
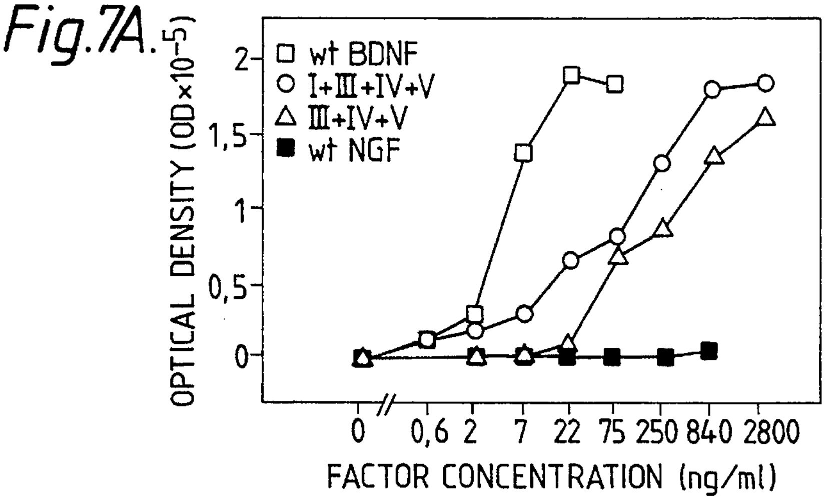
FIGS. 7A–C. Similar levels of TrkB receptor phosphorylation may result in different biological activities (see SEQ. ID. NOS. 1 and 2 for all chimera constructions). (A) Serial dilutions of transfected COS cell conditioned medium containing equal amounts of wt BDNF (□), wt NGF (■) and chimeric molecules I+III+IV+V (○) and III+IV+V (Δ) were assayed for their ability to stimulate tyrosine phosphorylation of TrkB expressed in rtrkB-3T3 cells. Appropriately exposed autoradiograms of phosphotyrosine blots were used for densitometric scanning and the results are expressed in arbitrary units of optical density. Similar results were obtained in a duplicate experiment. (B) Stimulation of neurite outgrowth from explanted E8 chick nodose ganglia in the presence of 50 ng/ml of wt BDNF, wt NGF and chimeric molecules I+III+IV+V and III+IV+V. Media from mock-transfected COS cells was used as a negative control (control). Results are presented as the mean of triplicate determinations ±SD. (C) Serial dilutions of transfected COS cell conditioned medium containing equal amounts of the indicated wt and chimeric molecules were assayed for their ability to stimulate survival of dissociated E8 chick nodose neurons. Results are presented as the mean of triplicate determinations ±SD.
Figure 7B:
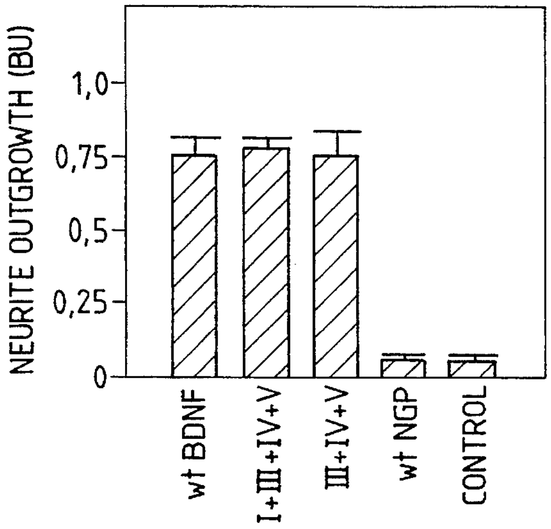
Figure 7C:
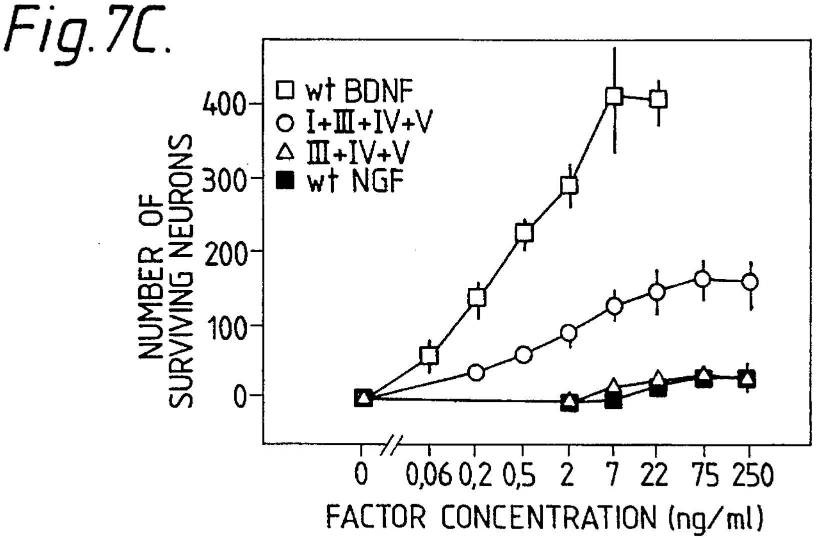

As shown in FIG. 7A, similar dose-response curves of receptor phosphorylation were obtained with wild-type BDNF and chimeric molecules I+III+IV+V and III+IV+V, although the latter two were displaced towards higher concentrations. In this assay, the $EC_{50}$ for wild-type BDNF was 5 ng/ml, whereas $EC_{50}$ for chimeric molecules I+III+IV+V and III+IV+V were 125 and 250 ng/ml, respectively (FIG. 7A). Despite these differences, both of the chimeric molecules and wild-type BDNF stimulated similar levels of neurite outgrowth from explanted nodose ganglia when assayed at concentrations ranging from 20 to 200 ng/ml (FIG. 7B and unpublished data). However, important differences were seen in their ability to promote neuronal survival of nodose neurons (FIG. 7C). Chimeric molecules III+IV+V failed to promote neuronal survival even at concentrations that allowed substantial levels of receptor phosphorylation (compare FIGS. 7A and 7C). On the other hand, chimeric molecule I+III+IV+V was able to rescue some neurons but it reached a plateau which was 3-fold lower than that of wild type BDNF, even though both molecules caused similar maximal levels of TrkB phosphorylation (compare FIGS. 7A and 7C). Comparison of FIGS. 7A, 7B and 7C shows that, when assayed at their respective $EC_{50}$ for receptor phosphorylation, all three molecules promote similar levels of neurite outgrowth while they differ widely in their ability to promote survival of the same neurons, suggesting that they induce different modes of receptor activation.

EXAMPLE 4. Engineering of a multifuctional neurotrophin agonist: Pan-Neurotrophin-1

The information obtained regarding structure-function relationships in NGF and BDNF was used to design a multifunctional neurotrophin agonist, referred to herein as pan-neurotrophin-1 (PNT-1). Since NT-3 is the only neurotrophin that binds to and activates TrkC, it was used as a skeleton (see SEQ. ID. NO. 1, 2 and 3 for chimera constructions). NT-3 also stimulates tyrosine phosphorylation of TrkB and, to a less extent, TrkA, although its efficiency to mediate biological effects through these receptors appear to be about 100-fold lower than BDNF or NGF (Cordon-Cardo, 1991; Klein, 1991 b; Squinto, 1991; Glass, 1991). In addition, NT-3 is structurally in an intermediate position between NGF and BDNF (Halbook, et al, 1991) and variable sequences in NT-3 contain features of functional importance in both NGF and BDNF (FIG. 1A). Based on our results with chimeric molecules, we tested the ability of $NH_2$-terminal sequences from NGF to improve NT-3 binding and activation of the TrkA receptor. Variable sequences from region V of BDNF were also introduced, in an attempt to enhance interaction with the TrkB receptor. Apart from the double chimera (PNT-1), single chimeric molecules (i.e. NGF $NH_2$/NT-3 and BDNF V/NT-3, respectively) were also constructed.

Figure 8A:
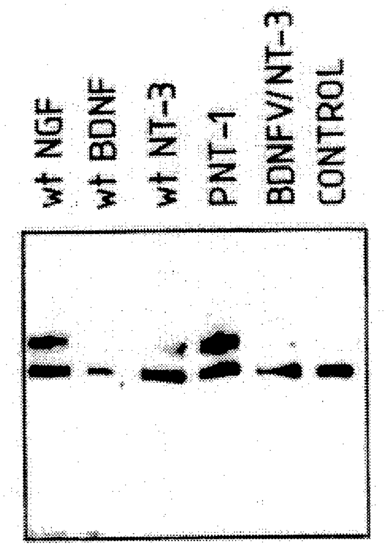
FIGS. 8A–D. PNT-1 interacts efficiently with TrkA, TrkB and TrkC receptors (see SEQ. ID. NOS. 1, 2 & 3 for all chimera constructions). (A), (B) and (C) Tyrosine phosphorylation of TrkA (A), TrkB (B) and TrkC (C) receptors stimulated by wt NGF, wt BDNF, wt NT-3 and the NT3-derived chimeric molecules PNT-1, BDNF V/NT-3 and NGF $NH_2$/NT-3. Trk-expressing cells were treated with 100 ng/ml of the indicated recombinant proteins and assayed for tyrosine phosphorylation. Arrowheads in A, B and C indicate the migration of phosphorylated TrkA (p $140^{trk}$), TrkB (p $145^{trkB}$) and TrkC (p$145^{trkC}$), respectively. (D) Serial dilutions of transfected COS cell conditioned medium containing equal amounts of wt NGF (□), wt NT-3 (○), and NT-3-derived chimeric molecules BDNF V/NT-3 (Δ) and PNT-1 (■) were assayed for their ability to displace $^{125}$I-NGF from receptors on rtrkA-3T3 cells. Medium from mock-transfected cells failed to displace $^{125}$I-NGF from these cells. Each point represents the mean of triplicate determinations. Standard deviation was at or generally below ±10%.
Figure 8B:
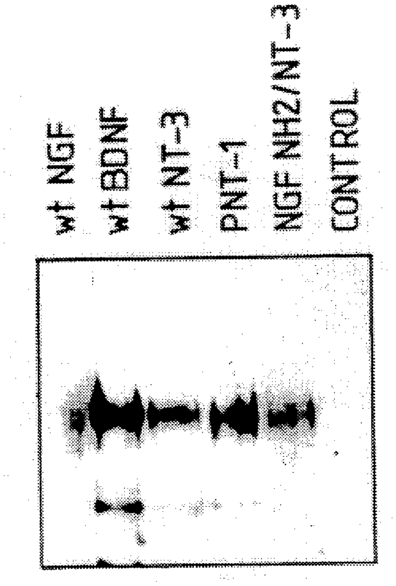
Figure 8C:
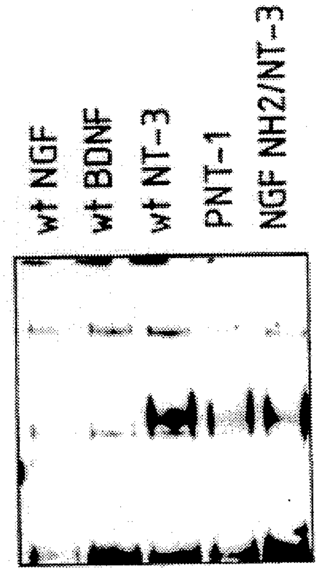
Figure 8D:
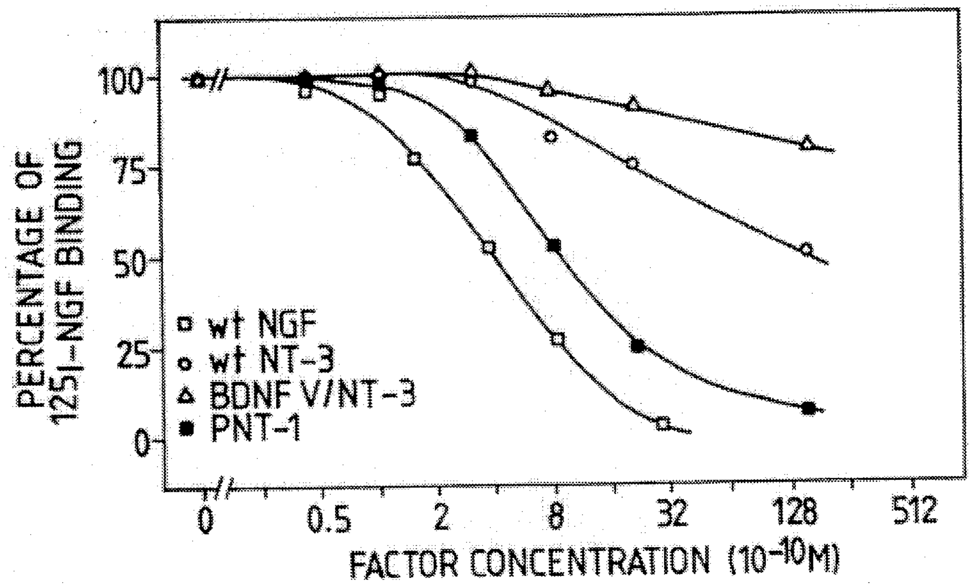

PNT-1 stimulated an efficient tyrosine phosphorylation of TrkA, B and C (FIGS. 8A, 8B and 8C, respectively). Phosphorylation of TrkA was significantly increased compared to wild type NT-3, and an increase was also seen in TrkB phosphorylation compared to wild-type NT-3. In general, PNT-1 activated Trk receptors at levels comparable to those obtained with each of their cognate wild type ligands. In addition, affinity of binding to TrkA receptors was improved in PNT-1 from about 3% (corresponding to wild-type NT-3) to almost 50% compared to wt NGF (FIG. 8D). Interestingly, the affinity of BDNF V/NT-3 was even lower than that of wild-type NT-3, in agreement with the notion that positive charges in region V interfere with binding to TrkA (FIG. 8D). Binding to TrkB was not changed in PNT-1 or BDNF V/NT-3 as compared to wild-type NT-3 (not shown).

Figure 9A:
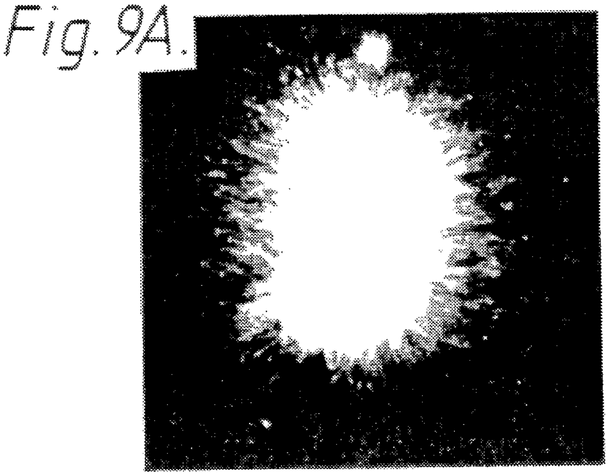
FIGS. 9A–G. PNT-1 displays multiple neurotrophic specificities. (A), (B), (C) and (D) Dark-field photomicrographs of E8 chick sympathetic ganglia cultured for 48 hr in the presence of COS cell conditioned media containing 2.5 ng/ml wt NGF (A), 20 ng/ml wt NT-3 (B), 20 ng/ml PNT-1 (C) and 20 ng/ml NGF $NH_2$/NT-3 (D). (E) Dose-response curves of neurite outgrowth stimulation of E8 chick sympathetic ganglia by wt NGF (□), wt NT-3 (□) and NT-3-derived chimeric molecules NGF $NH_2$/NT-3 (Δ) and PNT-1 (■). Data from three determinations varied by ±20% of the average values reported here. (F) Neuronal survival of dissociated E8 chick sympathetic neurons in the presence of 2 ng/ml of wt NGF, wt NT-3 and NT-3-derived chimeric molecules NGF $NH_2$/NT-3 and PNT-1. Media from mock-transfected COS cells was used as a negative control (control). Results are presented as the mean of triplicate determination ±SD. (G) Neuronal survival of dissociated E8 chick nodose neurons in the presence of saturating amounts (20–50 ng/ml) of wt BDNF, wt NGF, wt NT-3 and NT-3-derived chimeric molecules PNT-1 and BDNF V/NT-3. Media from mock-transfected COS cells was used as a negative control (control). Results are presented as the mean of triplicate determinations ±SD.
Figure 9B:
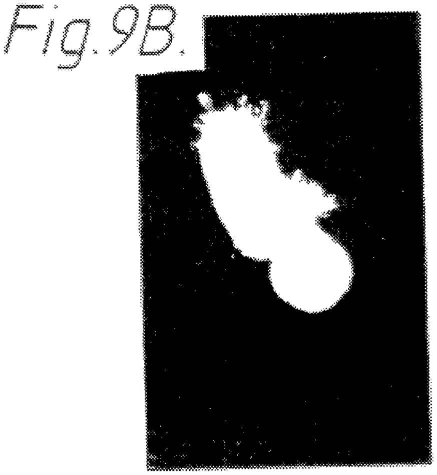
Figure 9C:
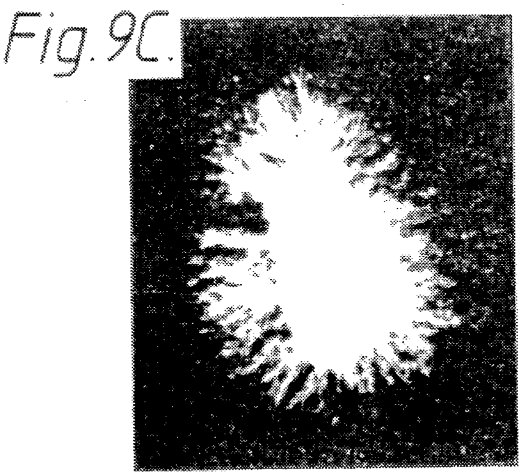
Figure 9D:
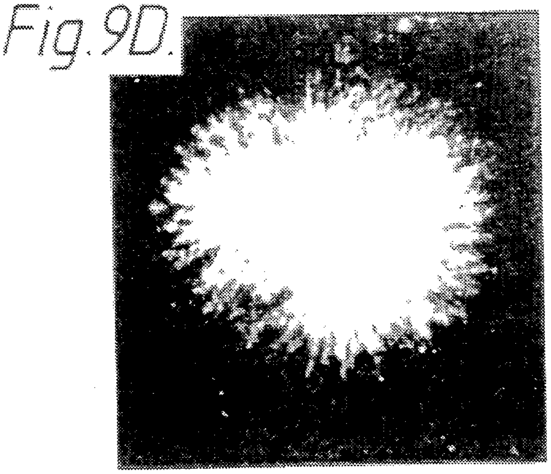
Figure 9E:
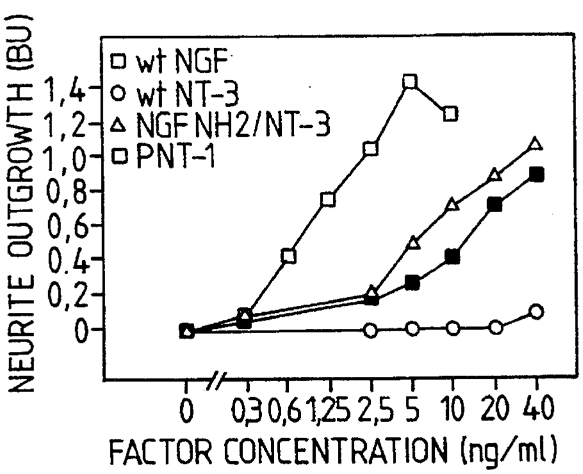
Figure 9F:
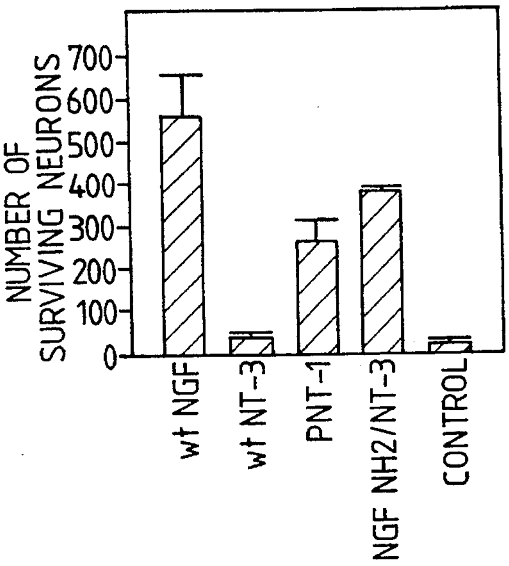

Biological activities of PNT-1 and related molecules were assayed in sympathetic neurons and in neurons from the nodose ganglion. Both PNT-1 and NGF $NH_2$/NT-3 efficiently stimulated neurite outgrowth from explanted sympathetic ganglia. In contrast, wild type NT-3 displayed only a marginal effect when assayed at high concentrations (compare FIGS. (9A, 9B, 9C and 9D). Comparison of dose-response curves showed a substantial increase of NGF-like biological activity in both PNT-1 and NGF $NH_2$/NT-3 compared to wild type NT-3. (FIG. 9E). When compared to wild type NGF, the potencies of NGF $NH_2$/NT-3 and PNT-1 were 8- and 15-fold lower, respectively. As suggested by the TrkA binding experiment (FIG. 8D), the differences in bioactivity between NGF $NH_2$/NT-3 and PNT-1 are probably due to a structural interference from region V of BDNF on the interaction with TrkA. The ability of PNT-1 to stimulate neurite outgrowth from sympathetic ganglia correlated with survival of dissociated sympathetic neurons (FIG. 9F), whereas no survival was seen with wild-type NT-3 (FIG. 9F).

Figure 9G:
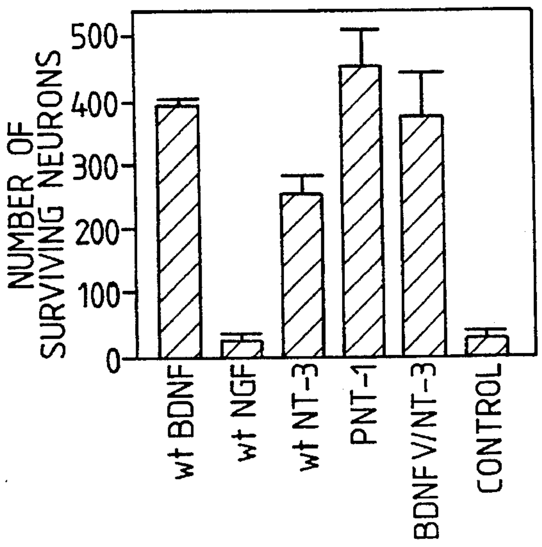

Previous studies have demonstrated additive effects of BDNF and NT-3 in the survival of nodose neurons, indicating that the two factors promote survival of different neuronal populations in this ganglion (Hohn, 1990; Gotz, 1992). The effects of PNT-1 on survival of nodose neurons was then assayed to evaluate the efficiency of this molecule as a BDNF and NT-3 agonist. As expected, wild-type NGF failed to rescue neurons from this ganglion, whereas saturating concentrations of wild type BDNF and wild type NT-3 rescued 40 and 25% respectively (FIG. 9G). PNT-1 promoted the survival of 45% of the nodose neurons, almost a 2-fold increase compared to NT-3 (FIG. 9G). Comparable survival effects were obtained with the BDNF V/NT-3 chimera, indicating that the increased activity was due to the replacement of region V in NT-3 with region V from BDNF. It should be noted, however, that the level of survival with PNT-1 did not reach the level expected for additive effects of BDNF and NT-3 (about 65%) (FIG. 9G), indicating that PNT-1 is a partial BDNF agonist.

EXAMPLE 5. Correlation with three dimensional structure of NGF

Figure 10A:
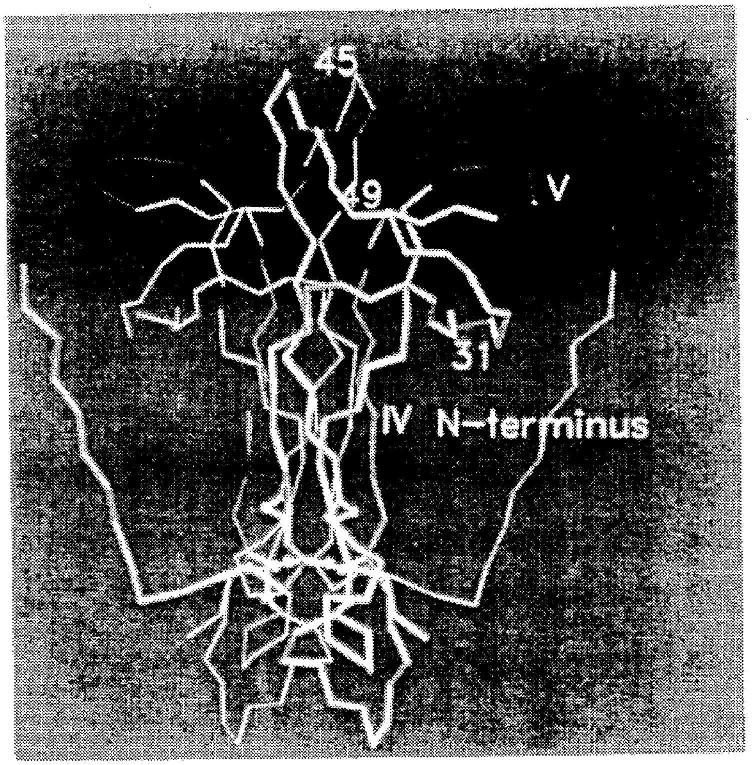
FIGS. 10A–D. Three-dimensional structure of the NGF receptor binding site to the TrkA receptor. (A) A $C_\alpha$ backbone diagram of the NGF dimer viewed perpendicular to the two-fold axis with the regions involved in Trk binding shown. One of the two symmetrically related Trk binding sites include regions I (lie-31), IV, V from the first protomer, and region II (residues 45 to 49) plus the $NH_2$-terminus from the second protomer (numbered in red). The $NH_2$-terminal chain (residues 1–10) is not seen in the crystal structure and it is shown here in an arbitrary extended conformation. Disulphide bridges at the bottom are shown. (B) A closer view of the top part of the NGF dimer in the same orientation as (A), with individual residues from one binding site numbered (with 500 added to the residue number compared with the first chain). (C) A view of the top part of the NGF dimer perpendicular to that in (B), along the two-fold axis. Residues contributing to each of the two binding sites align on a continuous plane stretching across the side of the dimer. Residues from one of the two binding sites are numbered as in (B), but their symmetry-related equivalents can also be identified. (D) The "middle" region of the NGF dimer in the same orientation as (B) showing the location of strand residues 79, 81, 84 on the edge of the first protomer. $NH_2$-terminal chain from the second monomer is shown in an arbitrary position, which also indicates that it is potentially capable of contacting region IV of the first protomer.
Figure 10B:
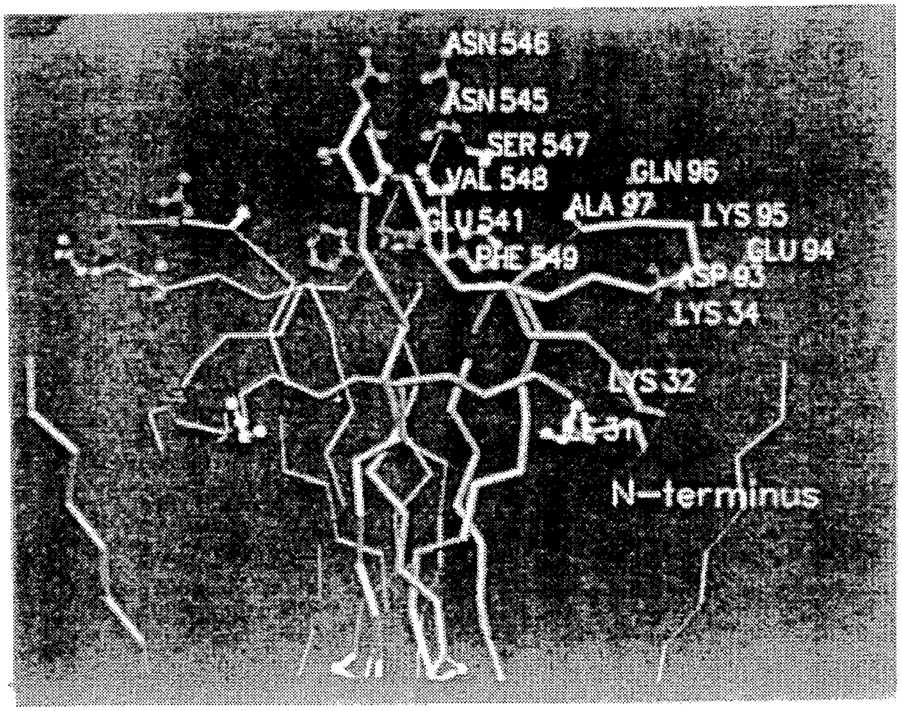
Figure 10C:
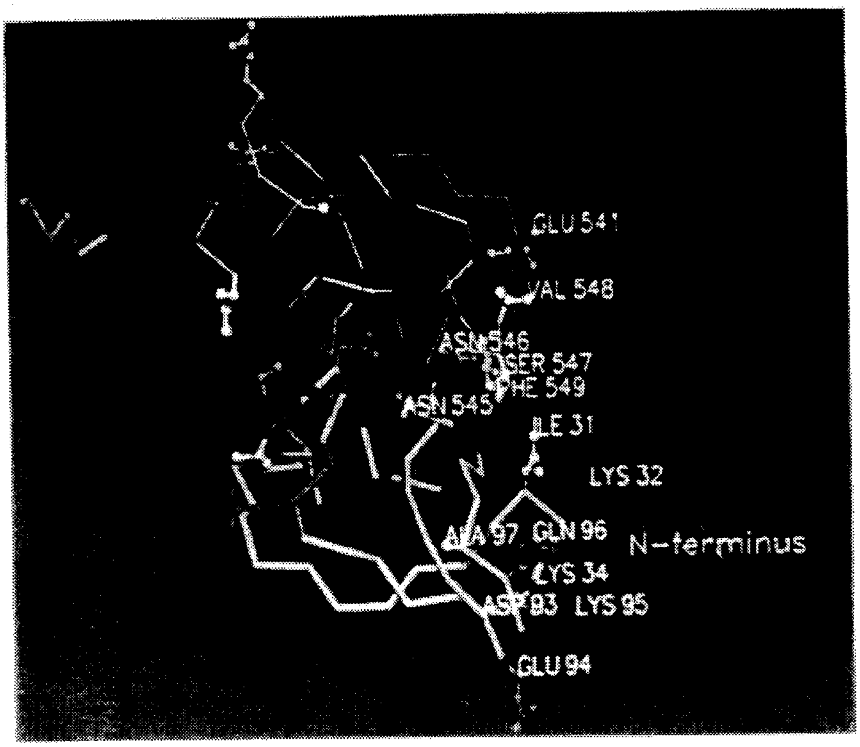
Figure 10D:
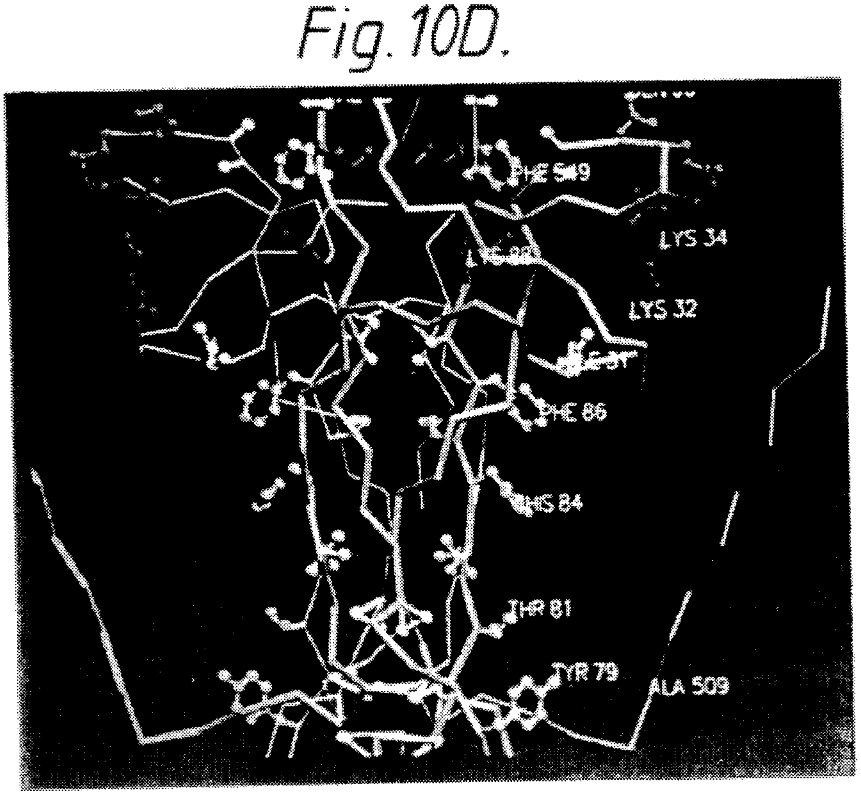

The location in the crystal structure of the NGF dimer (McDonald, 1991) of amino acid residues responsible for the interaction of neurotrophins with Trk receptors was examined by computer graphics. When these residues are viewed in the three-dimensional structure they delineate a continuous surface extending approximately parallel to the two fold axis of the NGF dimer (FIG. 10A). Regions I, IV and V from one protomer form a continuous surface down the side of the NGF dimer. At the top of the dimer this surface is in contact with region II from the other protomer (FIG. 10B). Looking from the top of the molecule along the two-fold axis, residues 31 to 34 (region I) and residues 95 to 97 (region V) from the first protomer and residues 41 and 45 to 49 (region II) from the second protomer align on a continuous plane stretching across the side of the NGF dimer (FIG. 10C). In the middle region of the NGF dimer, residues 79,81, and 84 (region IV) from the first protomer extend the binding surface down to about three quarters of the molecule (McDonald , 1991) and, although they can not be positioned with respect to the other regions of the molecule, it is tempting to speculate that they cooperate in the extension of the binding surface along the side of the dimer. Overall the binding site is a rather flat and elongated surface extending up to loop region II which protrudes out from the rest of the molecule and which conceivably could be buried in the receptor binding pocket.

DISCUSSION

We have previously defined five variable regions in which the NGF sequence differs from those of BDNF and NT-3 (FIG. 1A) (see SEQ. ID. NOS. 1, 2 and 3) (Ibáñez, 1991). Three of these regions (variable regions I, II and V) correspond to β-hairpin loops exposed on the surface of the NGF molecule, whereas region III contains a reverse turn and region IV is a β-strand (FIG. 1B) (McDonald, 1991). Using oligo-nucleotide site-directed mutagenesis, the variable regions in the NGF molecule were systematically replaced either alone or in different combinations by the corresponding sequences from BDNF. Chimeric molecules including sequences from BDNF $NH_2$- and COOH-termini were also constructed. In addition, point mutations were generated in either the wild-type (wt) NGF molecule or in the context of a chimeric molecule. The chimeric and mutant molecules were transiently expressed in COS cells and the yield of recombinant proteins was quantitated by SDS-PAGE of metabolically labeled polypeptides and by Western blotting. Serial dilutions of conditioned media containing equivalent amounts of the different recombinant proteins were then assayed in competitive receptor binding assays and receptor tyrosine phosphorylation assays using fibroblasts ectopically expressing TrkA or TrkB receptors (Kaplan, 1991; Soppet, 1991). Biological activity of the different molecules was assayed in cultures of NGF-responsive neurons from embryonic chick sympathetic ganglia and BDNF-responsive neurons from embryonic nodose ganglia. Structural elements involved in the interaction of NGF and BDNF with their respective TrkA and TrkB receptors were investigated simultaneously by evaluating the effect of the mutations as loss-of-NGF function and gain-of-BDNF function, respectively.

Receptor binding sites in neurotrophins to Trk receptors

Our study of structural determinants of binding and activation of Trk receptors by NGF and BDNF reveals multiple contacts that cooperate synergistically to receptor binding, receptor activation and biological activity. Amino acid residues mediating the interaction of NGF with TrkA were localized in the $NH_2$-terminus (residues 3 to 9), variable region I (notably Ile-31), variable region II, particularly Glu-41 and residues 45–49 (notably Asn-45) and variable regions IV and V (residues 94 to 98). Within variable region IV, Tyr-79, Thr-81 and His-84 are present in NGF from all species analyzed to date but are replaced by non-conservative residues in other neurotrophins (Halbook, 1991) suggesting that they could be mediating the interaction of NGF region IV with TrkA. Interestingly, structural elements mediating the interaction of BDNF with the TrkB receptor were, in general, localized in variable regions analogous to those involved in the interaction of NGF with TrkA. Thus, residues in variable regions I, IV and V were shown to interact with TrkB and promote receptor phosphorylation. In region V, Lys-96 and Arg-97 are responsible for this effect, whereas in region IV, Gln-84 appears to be important. Similarly, residues 45 to 49 in variable region II were implicated in TrkB binding and bioactivity in nodose neurons. A notable difference was however found for the $NH_2$-terminus, which seems to play a less important role for receptor binding in BDNF than in NGF. Further mutagenesis of these sequences in BDNF will be required to clarify their role in TrkB binding. Taken together, these results suggest that during evolution, neurotrophins have conserved a general mechanism of binding to their receptors, and that a parallel evolution of cognate ligands and Trks have developed specific contacts through different residues in the same variable regions of the neurotrophins.

The results obtained with chimeric molecules in the $NH_2$-terminus (residues 3 to 9) of NGF suggest that this region is more important for binding to TrkA than for activation or biological activity. The role of the other variable regions in receptor binding seems to be secondary and probably synergistic with the $NH_2$ terminus, by stabilizing the ligand-receptor complex. Due to the poor density of the $NH_2$-terminus on structural maps, it has been suggested that this region is both flexible and solvent accessible ([McDonald, 1991]). It is possible that the $NH_2$-terminal chain of NGF function as an anchor for initial receptor contact in a way analogous to that proposed for the COOH-terminus of the insulin β-chain ([Nakagawa, 1986]). This initial binding would then lead to further conformational changes in the ligand and/or receptor to optimize binding interactions and allow receptor activation.

Figure 11:
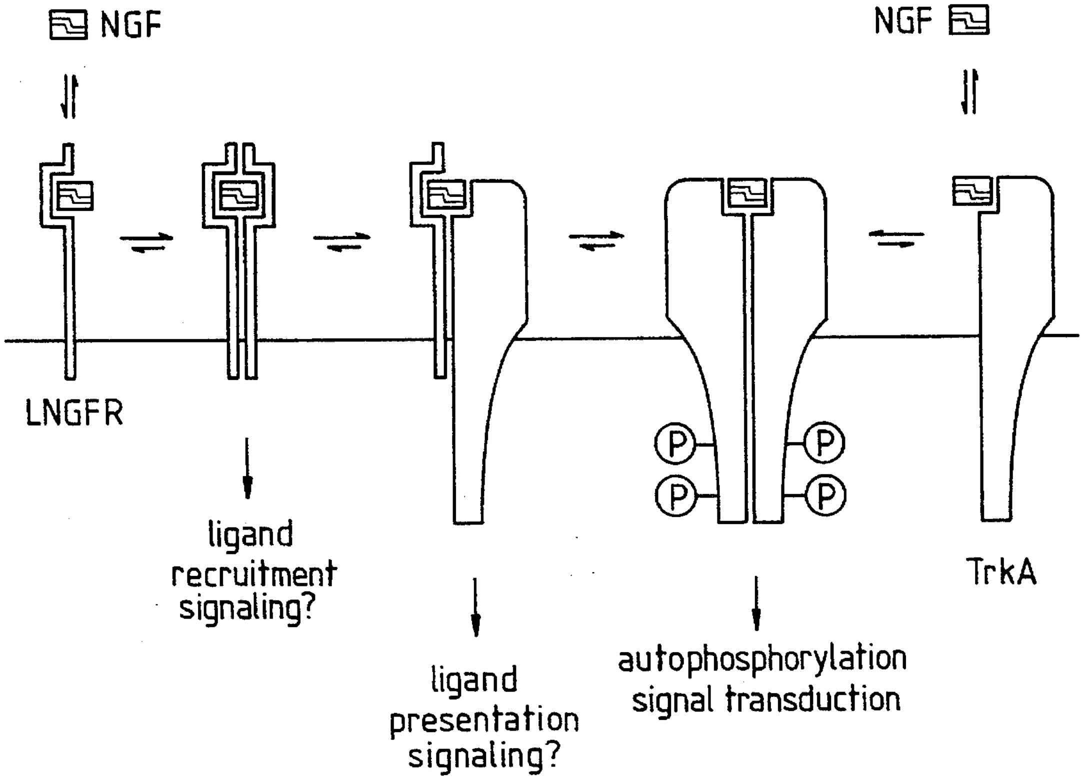
FIG. 11. Model for the dynamics of NGF receptor complexes on the membrane of responsive cells. Cross-linking experiments have so far only demonstrated the association of monomeric and homodimeric receptors with the ligand. The bivalent nature of the NGF dimer may allow the formation of heterodimeric receptor complexes which could be transient intermediates in the transfer of ligand from LNGGFR to TrkA. Active binding surfaces in the NGF dimer are labeled. The signaling capacity of homodimeric LNGFR and heterodimeric receptor complexes has yet to be demonstrated.

It is generally accepted that ligand-induced activation of tyrosine kinase receptors is mediated by receptor dimerization or oligomerization ([Schlessinger, 1988]). Cross-linking studies have revealed the formation of TrkA homodimers upon NGF binding to PC12 cells and fibroblasts ectopically expressing TrkA ([Meakin, 1991]; [Jing, 1992]). Recently, using kinase-deficient mutants of the TrkA receptor, Jing et al. (1992) demonstrated that formation of functional TrkA homodimers is necessary for NGF-mediated receptor autophosphorylation and signal transduction. Due to the two-fold symmetry of the NGF dimer, identical binding surfaces are formed on both sides of the molecule, each containing structural elements from both protomers (FIG. 10C). It is therefore conceivable that a bivalent NGF dimer could mediate dimerization of neighboring TrkA receptors. Binding of the NGF dimer to one TrkA molecule could then promote the association of the complex with a second molecule of TrkA through the remaining binding surface, resulting in receptor autophosphorylation and signal transduction (FIG. 11). Although validation of this model will require determination of the stoichiometry of the NGF-TrkA complex, similar models of ligand-induced tyrosine -kinase receptor dimerization have been proposed for other bivalent ligands like platelet-derived growth factor (PDGF) ([Heldin, 1989]; [Seifert, 1989]). In the case of PDGF, it was proposed that each PDGF monomer interacts with one distinct monomer of the receptor, whereas in the neurotrophins, both neurotrophin monomers seem to make contacts with each Trk receptor. The fact that native BDNF and NT-3 also appear to be dimeric molecules ([Radziejewski, 1992]) suggests that this model could be applied to all the neurotrophins.

Amino acid residues mediating binding of NGF to LNGFR have recently been identified ([Ibáñez, 1992]). Interestingly, these residues seem to partially overlap with the TrkA binding site identified in this study. Association between LNGFR and TrkA has been proposed as a necessary step for the formation of NGF high-affinity binding sites ([Hempstead, 1991), although results from other laboratories have recently disputed that model ([Klein, 1991]; [Jing, 1992]). Complexes between LNGFR and TrkA have so far not been detected in cross-linking experiments performed with either PC12 cells, fibroblasts or sensory neurons under conditions which allowed detection of LNGFR or TrkA homodimers ([Hosang, 1985]; [Meakin, 1991]; [Jing, 1992]. In our model, provided no steric impediments, binding of NGF to one molecule of TrkA or LNGFR still leaves one identical binding site free which could be used to form either a TrkA-LNGFR heterodimer or any of the two receptor homodimers. That receptor heterodimers have not yet been detected could be due to their very low number or to that they represent a transient state in the dynamics of NGF receptor complexes on the membrane of responsive cells (FIG. 11). It has been suggested that LNGFR contributes to the activation of Trk receptors by promoting ligand presentation or recruitment of circulating neurotrophins ([Glass, 1991]; [Jing, 1992]). Since the number of LNGFR in the membrane of responsive cells is about 10-fold higher than the number of TrkA molecules and NGF dissociates faster from LNGFR, it is possible that LNGFR-TrkA complexes function as intermediates in the transfer of ligand from LNGFR homodimers to TrkA homodimers (FIG. 11). The proportion of LNGFR and TrkA homo and heterodimers present in a cell could depend on the relative amount of each receptor species and on the membrane environment of a given cell type.

Upon ligand binding, activated TrkA homodimers autophosphorylate on specific tyrosine residues which are, in turn, supposedly recognized by intracellular proteins involved in signal transduction ([Kaplan, 1991]). In this context, the observation that similar levels of TrkB receptor phosphorylation can lead to different biological effects is intriguing and may reflect activation of different components in the signal transduction pathway. Thus, qualitative rather than quantitative differences could exist between states of receptor activation achieved after stimulation by different, although structurally-related ligands. These differences may be due to variations in the conformation of the receptor upon ligand binding or in the pattern of phosphotyrosines in the cytoplasmic domain of the receptor, or to both. The recent observation that distinct phosphotyrosines in the PDGF and fibroblast growth factor (FGF) receptor bind to specific molecules that mediate different signaling pathways ([Fantl, 1992]; [Peters, 1992]; [Mohammadi, 1992]) suggest that different phosphorylation patterns in Trk receptors could result in transduction of different biological signals such as neurite outgrowth or neuronal survival. Thus, chimeric molecules with different biological activities could be valuable tools to unravel the signal transduction pathways leading to the pleiotropic biological effects of neurotrophins.

TABLE 1

Relative TrkA receptor binding, receptor activation and specific biological activity of wild type, mutant and chimeric NGF proteins.

| Mutant Protein[a] | Receptor Binding[b] % of wild type | Receptor Activation[c] | Biological Activity[d] % of wild type |
|---|---|---|---|
| wt NGF | 100 | +++ | 100 |
| wt BDNF | <0,2 | – | <0,2 |
| NH2 | 23 | +++ | 100 |
| COOH | 90 | +++ | 100 |
| I31A | 20 | ND | 25 |

TABLE 1-continued

Relative TrkA receptor binding, receptor activation and specific biological activity of wild type, mutant and chimeric NGF proteins.

| Mutant Protein[a] | Receptor Binding[b] % of wild type | Receptor Activation[c] | Biological Activity[d] % of wild type |
|---|---|---|---|
| I + III + IV | 105 | +++ | 100 |
| III + IV + V | 95 | +++ | 50 |
| I + III + IV + V | 110 | ++ | 50 |
| NH2 + I + III + IV + V | <1 | – | <1 |
| NH2 + III + IV + V | 12 | ++ | 7 |
| NH2 + I + III + V | 12 | ++ | 35 |
| NH2 + I + III + IV | 22 | ++ | 40 |
| COOH + I + III + IV + V | 75 | ++ | 50 |
| I + IIa + III + IV + V | 110 | ++ | 50 |
| I + IIb + III + IV + V | 96 | ± | 10 |
| I + II + III + IV + V | 70 | – | 3 |
| E41A + I + III + IV + V | 90 | + | 12 |
| N43A + I + III + IV + V | 100 | +++ | 50 |
| I44A + I + III + IV + V | 90 | +++ | 50 |
| N45A + I + III + IV + V | 95 | ++ | 25 |
| N46A + I + III + IV + V | 100 | +++ | 50 |
| V48A + I + III + IV + V | 100 | +++ | 50 |

[a]Mutants are abbreviated by the wt residue (single amino acid designation), followed by its codon number and the mutant residue. Roman numerals denote variable regions in chimeric molecules that were replaced by homologous regions from BDNF.
[b]Data from at least three different dose-response experiments using rtrkA-3T3 cells varied by ±10%.
[c]Measured as receptor tyrosine phosphorylation stimulated by 100 ng/ml of ligand. Consistent results were obtained in three independent experiments.
[d]Measured as neurite outgrowth evoked from explants of embryonic sympathetic ganglia. Data from at least three different dose-response experiments varied by ±10%.
ND, not determined.

TABLE 2

Relative TrkB receptor binding, receptor activation and specific biological activity of wild type, mutant and chimeric NGF proteins.

| Mutant Protein[a] | Receptor Binding[b] % of wild type | Receptor Activation[c] | Biological Activity[d] % of wild type |
|---|---|---|---|
| wt BDNF | 100 | +++ | 100 |
| wt NGF | <0,2 | – | <5 |
| NH2 | <0,2 | – | ND |
| I | ND | + | ND |
| II[e] | ND | – | ND |
| III | ND | – | ND |
| IV | ND | + | ND |
| Y79Q + T81R | ND | – | ND |
| V | ND | + | ND |
| Q96KR | ND | + | ND |
| COOH | ND | – | ND |
| I + V | ND | ++ | <5 |
| III + IV | ND | + | ND |
| III + V | ND | + | ND |
| I + III + IV | 0,3 | ++ | <5 |
| III + IV + V | 0,6 | ++ | <5 |
| I + III + IV + V | 1,2 | +++ | 30 |
| NH2 + I + III + IV + V | 2,5 | ND | 30 |
| COOH + I + III + IV + V | 1 | ND | 30 |
| I + IIa + III + IV + V | 12 | ND | 30 |
| I + IIb + III + IV + V | 12 | ND | 60 |
| I + II + III + IV + V | 55 | ND | 80 |

[a]Mutants and chimeric molecules are abbreviated as in Table 1.
[b]Data from at least three dose-response experiments using rtrkB-3T3 cells varied by ±10%.
[c]Measured as receptor tyrosine phosphorylation stimulated by 100 ng/ml of ligand. Consistent results were obtained in three independent experiments.
[d]Measured as maximal cell survival in cultures of disociated embryonic nodose neurons. Data from at least three experiments varied by ±10%.
[e]Yield of recombinant protein lower than 0,5% of wt NGF. Assayed at 10 ng/ml.
ND, not determined.

REFERENCES

Barde, Y.-A., Edgar, D. and Thoenen, H. (1982). Purification of a new neurotrophic factor from mammalian brain. EMBO J. 1,549–553.

Berkemeier, L., Winslow, J., Kaplan, D., Nicolics, K., Goeddel, D. and Rosenthal, A. (1991). Neurotropin-5: A novel neurotropic factor tat activates trk and trkB. Neuron 7, 857–866.

Cordon-Cardo, C., Tapley, P., Jing, S., Nanduri, V., O'Rourke, E., Lambelle, F., Kovary, K., Klein, R., Jones, K., Reichardt, L. and Barbacid, M. (1991). The trk tyrosine kinase mediates the mitogenic properties of nerve growth factor and neurotrophin-3. Cell 66, 173–183.

Daopin, S., Piez, K., Ogawa, Y. and Davies, D. (1992). Crystal structure of transforming growth factor-β2: an unusual fold for the superfamily. Science 257, 369–373.

Ebendal, T. (1989). In Nerve Growth Factors, R. A. Rush, ed. (Chichester: John Wiley & Sons), pp. 81–93.

Ernfors, P., Ibáñez, C. F., Ebendal, T., Olson, L. and Persson, H. (1990). Molecular cloning and neurotrophic activities of a protein with structural similarities to β-nerve growth factor: developmental and topographical expression in the brain. Proc. Natl. Acad. Sci. USA 87, 5454–5458.

Fantl, W., Escobedo, J., Martin, G., Turck, C., del Rosario, M., McCormick, F. and Williams, L. (1992). Distinct phosphotyrosines on a growth factor receptor bind to specific molecules that mediate different siganling pathways. Cell 69, 413–423.

Glass, D., Nye, S., Hantzopoulos, P., Macchi, M., Squinto, S., Goldfarb, M. and Yancopoulos, G. (1991). TrkB mediates BDNF/NT-3-dependent survival and proliferation of fibroblasts lacking the low affinity NGF receptor. Cell 66, 405–413.

Götz, R., Kolbeck, R., Lottspeich, F. and Barde, Y. A. (1992). Production and characterization of recombinant mouse neurotrophin-3. Eur. J. Biochem. 204, 745–9.

Hallböök, F., Ibáñez, C. F. and Persson, H. (1991). Evolutionary studies of the nerve growth factor family reveal a novel member abundantly expressed in Xenopus ovary. Neuron 6, 845–858.

Heldin, C. H., Ernlund, A., Rorsman, C. and Rönnstrand, L. (1989). Dimerization of B-type platelet-derived growth factor receptors occurs after ligand binding and is closely associated with receptor kinase activation. J Biol Chem 264, 8905–12.

Hempstead, B., Martin-ZAnca, D., Kaplan, D., Parada, L. and Chao, M. (1991). High-affinity NGF binding requires coexpression of the trk proto-oncogene and the low-affinity NGF receptor. Nature 350, 678–683.

Hempstead, B. L., Schleifer, L. S. and Chao, M. V. (1989). Expression of functional nerve growth factor receptors after gene transfer. Science 243, 373–375.

Hofer, M., Pagliusi, S. R., Hohn, A., Leibrock, J. and Barde, Y.-A. (1990). Regional. distribution of brain-derived neurotrophic factor in the adult mouse brain. EMBO J. 9, 2459–2464.

Hohn, A., Leibrock, J., Bailey, K. and BArde, Y.-A. (1990). Identification and characterization of a novel member of the nerve greowth factor/brain-derived neurotrophic factor family. Nature 344, 339–341.

Hosang, M. and Shooter, E. M. (1985). Molecular characteristics of nerve growth factor receptors on PC12 cells. J Biol Chem 260, 655–62.

Ibáñez, C. F., Hallböök, F., Ebendal, T. and Persson, H. (1990). Structure-function studies of nerve growth factor: functional importance of highly conserved amino acid residues. EMBO J. 9, 1477–1483.

Ibáñez, C., Ebendal, T. and Persson, H. (1991a). Chimeric molecules with multiple neurotrophic activities reveal structural elements determining the specificities of NGF and BDNF. EMBO J. 10, 2105–2110.

Ibáñez, C. F., Hallböök, F., Söderström, S., Ebendal, T. and Persson, H. (1991b). Biological and immunological properties of recombinant human, rat and chicken nerve growth factors: a comparative study. J. Neurochem. 57, 1033–1041.

Ibáñez, C. F., Ebendal, T., Barbany, G., Murray-Rust, J., Blundell, T. L. and Persson, H. (1992). Disruption of the Low Affinity Receptor-Binding Site in NGF Allows Neuronal Survival and Differentiation by Binding to the trk Gene Product. Cell 69, 329–341.

Ip, N.Y., Ibáñez, C. F., Nye, S. H., McClain, J., Jones, P. F., Gies, D. R., Bellusdo, L., Le Beau, M. M., Espinosa III, R., Squinto, S. P., Persson, H. and Yancopoulos, G. (1992). Mammalian neurotrophin-4: structure, chromosomal localization, tissue distribution and receptor specificity. Proc Natl Acad Sci USA 89, 3060–3064.

Jing, S., Tapley, P. and BArbacid, M. (1992). Nerve growth factor mediates signal transduction through Trk homodimer receptors. Neuron in press, Johnson, D., Lanahan, A., Buck, C. R., Sehgal, A., Morgan, C., Mercer, E., Bothwell, M. and Chao, M. (1986). Expression and structure of the human NGF receptor. Cell 47, 545–554.

Jones, K. R. and Reichardt, L. F. (1990). Molecular cloning of a human gene that is a member of the nerve growth factor family. Proc. Natl. Acad. Sci. USA 87, 8060–8064.

Kaisho, Y., Yoshimura, K. and Nakahama, K. (1990). Cloning and expression of a cDNA encoding a novel human neurotropic factor. FEBS Lett. 266, 187–191.

Kaplan, D., Hempstead, B., Martin-Zanca, D., Chao, M. and Parada, L. (1991). The trk proto-oncogene product: a signal transducing receptor for nerve growth factor. Science 252, 554–558.

Kaplan, D., Martin-Zanca, D. and Parada, L. (1991). Tyrosine phosphorylation and tyrosine kinase activity of the trk proto-oncogene product induced by NGF. Nature 350, 158–160.

Klein, R., Jing, S., Nanduri, V., O'Rourke, E. and Barbacid, M. (1991). The trk protooncogene encodes a receptor for nerve growth factor. Cell 65, 189–197.

Klein, R., Lamballe, F., Bryant, S. and Barbacid, M. (1992). The trkB tyrosine protein kinase is a receptor for Neurotrophin-4. Neuron 8, 947–956.

Klein, R., Nanduri, V., Jing, S., Lambelle, F., Tapley, P., Bryant, S., Cordon-Cardo, C., Jones, K., Reichardt, L. and Barbacid, M. (1991). The trkB tyrosine kinase is a receptor for brain-derived neurotrophic factor and neurotrophin-3. Cell 66, 395–403.

Kunkel, T. (1985). Rapid and efficient site-specific mutagenesis without phenotypic selection. Proc. Natl. Acad. Sci. USA 82, 488–492.

Lambelle, F., Klein, R. and Barbadd, M. (1991). trkC, a new member of the trk family of tyrosine protein kinases, is a receptor for neurotrophin-3. Cell 66, 967–979.

Leibrock, J., Lottspeich, A. H., Hofer, M., Hengerer, B., Masiakowski, P., Thoenen, H. and Barde, Y.-A. (1989). Molecular cloning and expression of brain-derived neurotrophic factor. Nature 341,149–52.

Levi-Montalcini, R. and Angeletti, P. (1968). Nerve growth factor. Physiol. Rev. 48, 534–569.

Lindsay, R. M., Thoenen, H. and Barde, Y.-A. (1985). Placode and neural crest-derived sensory neurons are responsive at early developmental stages to brain-derived neurotrophic factor. Dev. Biol. 112, 319–328.

Luthman, H. and Magnusson, G. (1983). High efficiency polyoma DNA transfection of chloroquine treated cells. Nucl. Acids Res. 11, 1295–1305.

Maisonpierre, P. C., Belluscio, L., S, S., Ip, N.Y., Furth, M. E., Lindsay, R. M. and Yancopoulos, G. D. (1990). Neurotrophin-3: A neurotrophic factor related to NGF and BDNF. Science 247, 1446–1451.

McDonald, N., Lapatto, R., Murray-Rust, J., Gunning, J., Wlodawer, A. and Blundell, T. (1991). New protein fold revealed by a 2.3-Å resolution crystal structure of nerve growth factor. Nature 354, 411–414.

Meakin, S. and Shooter, E. (1991). Molecular investigations on the high-affinity nerve growth factor receptor. Neuron 6, 153–163.

Mohammadi, M.,-Dionne, C., Li, W., Li, N., Spivak, T., Honegger, A., Jaye, M. and Schlessinger, J. (1992). Point mutation in FGF receptor eliminates phosphatidylinositol hydrolysis without affecting mitogenesis. Nature 358, 681–684.

Nakagawa, S. and Tager, H. (1986). Role of the phenylalanine B25 side chain in directing insulin interaction with its receptor. J Biol Chem 261, 7332–7341.

Oefner, C., D'Arcy, A., Winkler, F., Eggimann, B. and Hosang, M. (1992). Crystal structure of human platelet-derived growth factor BB. EMBO J 11, 3921–3926.

Peters, K., Marie, J., Wilson, E., Ives, H., Escobedo, J., Del Rosario, M., Mirda, D. and Williams, L. (1992). Point mutation of an FGF receptor abolishes phosphatidylinositol turnover and $Ca^{2+}$ flux but not mitogenesis. Nature 358, 678–681.

Radeke, M. J., Misko, T. P., Hsu, C., Herzenberg, L. A. and Shooter, E. M. (1987). Gene transfer and molecular cloning of the rat nerve growth factor receptor. Nature 325, 593–597.

Radziejewski, C., Robinson, R. C., DiStefano, P. S. and Taylor, J. W. (1992). Dimeric structure and conformational stability of brain-derived neurotrophic factor and neurotrophin-3. Biochemistry 31, 4431–4436.

Rodriguez-Tébar, A., Dechant, G. and Barde, Y.-A. (1990). Binding of brain-derived neurotrophic factor to the nerve growth factor receptor. Neuron 4, 487–492.

Rodriguez-Tebar, A., Dechant, G., Gotz, R. and Barde, Y. A. (1992). Binding of Neurotrophin-3 to its neuronal receptors and interactions with nerve growth Factor and brain-derived neurotrophic factor. EMBO J 11,917–922.

Rosenthal, A., Goeddel, D. V., Nguyen, T., Lewis, M., Shih, A., Laramee, G. R., Nikolics, K. and Winslow, J. W. (1990). Primary structure and biological activity of a novel human neurotrophic factor. Neuron 4, 767–773.

Sanger, F., Nicklen, S. and Coulson, A. R. (1977). DNA sequencing with chain-terminating inhibitors. Proc. Natl. Acad. Sci. USA 74, 5463–5467.

Schlessinger, J. (1988). Signal transduction by allosteric receptor oligomerization. Trends Biochem Sci 13, 443–447.

Sclunegger, M. and Grater, M. (1992). An unusual feature revealed by the crystal struture at 2.2Å resulution of human transforming growth factor-J32. Nature 358, 430–434.

Seifert, R. A., Hart, C. E., Phillips, P. E., Forstrom, J. W., Ross, R., Murray, M. J. and Bowen, P. D. (1989). Two different subunits associate to create isoform-specific platelet-derived growth factor receptors. J Biol Chem 264, 8771–8.

Soppet, D., Escandon, E., Maragos, J., Middlemas, D., Reid, S., Blair, J., Burton, L., Stanton, B., Kaplan, D., Hunter, T., Nikolics, K. and Parada, L. (1991). The neurotrophic factors brain-derived neurotrophic factor and neurotrophin-3 are ligands for the trkB tyrosina kinase receptor. Cell 65, 895–903.

Squinto, S., Stitt, T., Aldrich, T., Davis, S., Bianco, S., Radziejewski, C., Glass, D., Masiakowski, P., Furth, M., Valenzuela, D., DiStefano, P. and Yancopoulos, G. (1991). trkB encodes a functional receptor for brain-derived neurotrophic factor and neurotrophin-3 but not nerve grwoth factor. Cell 65, 885–893.

Suter, U., Angst, C., Tien, C. L., Drinkwater, C. C., Lindsay, R. M. and Shooter, E. M. (1992). NGF/BDNF Chimeric Proteins—Analysis of Neurotrophin Specificity by Homolog-Scanning Mutagenesis. J Neurosci 12, 306–318.

Thoenen, H., Bandtlow, C. and Heumann, R. (1987). The physiological function of nerve growth factor in the central nervous system: comparison with the periphery. Rev. Physiol. Biochem. Pharmacol. 109, 145–178.

Thoenen, H. and Barde, Y. A. (1980). Physiology of nerve growth factor. Physiol. Rev. 60, 1284–1325.

Ullrich, A. and Schlessinger, J. (1990). Signal transduction by receptors with tyrosine kinase activity. Cell 61,203–212.

Weskamp, G. and Reichardt, L. (1991). Evidence that biological activity of NGF is mediated through a novel subclass of high affinity receptors. Neuron 6, 649–663.

Whittemore, S. R., Friedman, P. L., Larhammar, D., Persson, H., Gonzalez, C. M. and Holets, V. R. (1988). Rat beta-nerve growth factor sequence and site of synthesis in the adult hippocampus. J. Neurosci. Res. 20, 403–410.

Yan, H., Schlessinger, J. and Chao, M. (1991). Chimeric NGF-EGF receptors define domains responsible for neuronal differentiation. Science 252, 561–564.

Yang, Y. C., Ciarlette, A. B., Temple, P. A., Chung, M. P., Kovacic, S., Witek-Gianotti, J. S., Leary, A. C., Kritz, R., Donahue, R. E., Wong, G. G. and Clark, S.C. (1986). Human IL-3 (multi-CSF): identification by expression cloning of a novel hematopoietic growth factor related to murine IL-3. Cell 47, 3–10.

It is claimed:

1. A chimeric neurotrophin comprising a neurotrophin selected from the group consisting of BDNF and NT-3 wherein amino acids 3–9 of said selected neurotrophin are replaced with amino acids 3–9 of NGF.

2. The chimeric neurotrophin of claim 1 wherein said selected neurotrophin is NT-3.

3. An NT-3 chimera comprising an NT-3 molecule wherein variable region V of the NT-3 molecule is replaced with variable region V from BDNF and amino acids 3–9 of the NT-3 molecule are replaced with amino acids 3–9 of NGF.

4. An NT-3 chimera comprising an NT-3 molecule wherein variable region V of said NT-3 molecule is replaced with variable region V of BDNF.

* * * * *